US011006866B2

(12) United States Patent
Baumann et al.

(10) Patent No.: US 11,006,866 B2
(45) Date of Patent: May 18, 2021

(54) DEVICE FOR MEASURING THE CONCENTRATION OF AN ANALYTE IN THE BLOOD OR TISSUE OF AN ANIMAL OR A HUMAN, PARTICULARLY A PREMATURE INFANT, IN A SELF-CALIBRATING MANNER

(71) Applicants: UNIVERSITAT ZURICH, Zurich (CH); EIDGENOSSISCHE MATERIALPRUFUNGS—UND FORSCHUNGSANSTALT, Dubendorf (CH)

(72) Inventors: Lukas Baumann, Zurich (CH); Katrin Scholler, St. Gallen (CH); Markus Rothmaier, Illnau (CH); Lukas Scherer, Basel (CH); Rene Rossi, Wil (CH); Damien Paul Joseph Henri De Courten, Tannay (CH); Martin Wolf, Zurich (CH)

(73) Assignees: UNIVERSITAT ZURICH, Zurich (CH); EIDGENOSSISCHE MATERIALPRUFUNGS—UND FORSCHUNGSANSTALT, Dubendorf (CH)

( * ) Notice: Subject to any disclaimer, the term of this patent is extended or adjusted under 35 U.S.C. 154(b) by 522 days.

(21) Appl. No.: 15/326,042

(22) PCT Filed: Jul. 14, 2015

(86) PCT No.: PCT/EP2015/066089
§ 371 (c)(1),
(2) Date: Jan. 13, 2017

(87) PCT Pub. No.: WO2016/008898
PCT Pub. Date: Jan. 21, 2016

(65) Prior Publication Data
US 2017/0202492 A1    Jul. 20, 2017

(30) Foreign Application Priority Data

Jul. 14, 2014    (EP) .................................. 14176976

(51) Int. Cl.
*A61B 5/145*    (2006.01)
*A61B 5/00*    (2006.01)

(52) U.S. Cl.
CPC ........ *A61B 5/14532* (2013.01); *A61B 5/0002* (2013.01); *A61B 5/0022* (2013.01); *A61B 5/1451* (2013.01); *A61B 2503/045* (2013.01)

(58) Field of Classification Search
CPC . A61B 5/14532; A61B 5/0022; A61B 5/0002; A61B 5/1451; A61B 2503/045
See application file for complete search history.

(56) References Cited

U.S. PATENT DOCUMENTS 5,139,023 A    8/1992 Stanley et al.
5,337,747 A    8/1994 Neftel
(Continued)

FOREIGN PATENT DOCUMENTS

CN    103890564    6/2014
JP    1986-025541    2/1986
JP    H04506919    12/1992

OTHER PUBLICATIONS

Keiichi Kimura and Yoshio Nakahara, "Analytical and Separation Chemistry by Taking Advantage of Organic Photochromism Combined with Macrocyclic Chemistry", Analytical Sciences, https://pdfs.semanticscholar.org/d684/f174d6db2dec8774a8cb1f6a3b416315e2b5.pdf (Year: 2009).*

(Continued)

*Primary Examiner* — Eric F Winakur
*Assistant Examiner* — Abid A Mustansir
(74) *Attorney, Agent, or Firm* — JMB Davis Ben-David

(57) ABSTRACT

The invention relates to a device for measuring the concentration of an analyte in the blood or tissue of a an animal or
(Continued)

a human, particularly a premature infant, wherein for measuring said concentration the device comprises a means (30) comprising at least a first and a second permeability with respect to said analyte, wherein the first permeability for said analyte differs from the second permeability for the analyte. Further, the invention relates to a corresponding method.

17 Claims, 31 Drawing Sheets

(56) References Cited

U.S. PATENT DOCUMENTS

| | | | |
|---|---|---|---|
| 2004/0072358 A1* | 4/2004 | Ballerstadt | A61B 5/14532 436/95 |
| 2005/0154272 A1 | 7/2005 | Holger et al. | |
| 2006/0004271 A1* | 1/2006 | Peyser | A61B 5/14521 600/362 |
| 2008/0241966 A1* | 10/2008 | Kunnecke | A61B 5/1486 436/536 |
| 2013/0253295 A1 | 9/2013 | Tolosa et al. | |
| 2014/0370509 A1 | 12/2014 | Wild et al. | |

OTHER PUBLICATIONS

Lukas Baumann et al: "Development of light-responsive porous polycarbonate membranes for controlled caffeine delivery", RSC Advances, vol. 3, No. 45, Jan. 1, 2013, p. 23317.

Nico Bruns et al: "Nanophase Separated Amphiphilic Conetwork Coatings and Membranes", Macromolecules, vol. 38, No. 6, Mar. 1, 2005, pp. 2431-2438.

Damien De Courten et al: "Opto-Fluidic Chip for Continuous Inline Monitoring of Glucose with Kinetic Enzymatic Fluorescence Detection", Procedia Engineering, vol. 47, Sep. 9, 2012, pp. 1203-1206.

Yoshihiro Ito, Providing material permeability in response to stimulation to porous membranes by grafting a polymer brush, Kobunshi Ronbunshu, Japan, The Society of Polymer Science, 1998, vol. 55, No. 4, pp. 171-181.

\* cited by examiner

100 μm

Dialysate extraction fraction

**Dialysate extraction fraction
for different microdialysis chamber heights**

DEVICE FOR MEASURING THE CONCENTRATION OF AN ANALYTE IN THE BLOOD OR TISSUE OF AN ANIMAL OR A HUMAN, PARTICULARLY A PREMATURE INFANT, IN A SELF-CALIBRATING MANNER

CROSS-REFERENCE TO RELATED APPLICATIONS

This is the U.S. National Stage of International Application No. PCT/EP2015/066089 filed Jul. 14, 2015, which was published in English under PCT Article 21(2), and which in turn claims the benefit of European Patent Application No. 14176976.0 filed Jul. 14, 2014.

The invention relates to a device for measuring the concentration of an analyte in the blood or tissue of an animal or a human, particularly in the blood or tissue of a premature infant, as well as to a corresponding method.

No commercial, non-invasive glucose monitoring device is available today for newborns (and adults). Every single neonate that is very preterm (e.g. less than 34 weeks gestational age GA) or too small for gestational age, needs frequent blood glucose measurements. This can currently only be achieved by invasively taking a blood sample and measuring the blood glucose externally. Taking blood samples has several undesired and potentially hazardous side effects. For instance, it causes anemia because the blood volume of preterm infants is as small as 80 ml/kg body weight. Blood sampling is also painful for the preterm babies. Repeated pain has bad clinical outcomes, and should be decreased. It also involves the risk of infections both for personnel and infant. Thus our invention is clinically relevant. In addition, these disadvantages inhibit measuring the blood glucose as frequently as clinically desirable. Since blood glucose can change rapidly, a continuous measurement would be clinically relevant.

A known non-invasive method for determining analytes in the blood or tissue is the sampling of ex-vivo body fluids transdermally (herein, ex-vivo means that the body fluid stems from the body). These fluids can then be analyzed without taking biocompatibility into account. Their analysis is not affected by tissue structure, nor by tissue inflammatory response to a foreign implanted analysis means. Also ex-vivo fluids contain much less interfering molecules as their in-vivo counterpart because substances with a large molecular weight are not collected (since the skin acts as a filter). Therefore, the ex-vivo measurement might be much more accurate than in vivo. But they need a calibration because of the varying skin properties. The relation between the blood analyte and its amount diffused through the skin is unknown.

Based on the above, the problem underlying the present invention is to provide an improved device and a method of the afore-mentioned kind that particularly allow to determine the concentration of an analyte in the blood of the patient in a simple manner, particularly without the need of taking blood samples.

This problem is solved by a device having the features of claim 1. Preferred embodiments are stated in the corresponding sub claims.

According to claim 1, the device for measuring the concentration of an analyte in the blood or tissue of an animal or a human, which analyte passively diffused through the skin of said person (or animal), particularly a premature infant, comprises a means comprising at least a first and a second permeability (e.g. corresponding to a first and a second state of e.g. a membrane) with respect to said analyte, wherein the first permeability for said analyte differs from the second permeability for the analyte.

This allows in principle a measurement of the concentration of the desired analyte in the blood or tissue of the animal or the human in a self-calibrating manner.

According to a preferred embodiment the probe head comprises a membrane that is designed to be (reversibly) switched between a first state, in which said membrane comprises said first permeability with respect to said analyte, and a second state, in which said membrane comprises said second permeability with respect to said analyte, wherein the first permeability is different from the second permeability, such that the analyte, which e.g. passively diffused through the skin of said animal or human, is able to diffuse through said membrane when the membrane resides in the first state and the probe head contacts the skin, and such that the analyte is able to diffuse through said membrane when the membrane resides in the second state and the probe head contacts the skin of the person.

Further, alternatively, the probe head (or probe head means) comprises a (first) membrane and a further (second) membrane, wherein the membrane comprises a first permeability with respect to said analyte, and wherein the further membrane comprises a second permeability with respect to said analyte, wherein the first permeability is different from the second permeability, such that said analyte, which e.g. passively diffused through the skin of said animal or human, is able to diffuse through said membrane when the probe head contacts the skin, and such that said analyte is able to diffuse through said further membrane when the probe head contacts the skin of the person.

Possible analytes are most preferably glucose, but also caffeine, urea, cortisone, hydrocortisone, lactate, opioids, cocaine, ammonia, creatinine, bilirubin, or all molecules that penetrate the untreated or even treated skin.

The present solution according to invention allows a self-calibrating measurement of the concentration of the desired analyte (e.g. glucose) in the blood of the patient in advantageous manner as will be shown below.

According to a preferred embodiment of the present invention (in case a membrane having said two states is employed) the device preferably comprises a switching means for switching said membrane between said two states.

In an embodiment of the invention, such a switching means is designed to irradiate the membrane with electromagnetic radiation, particularly light, for switching the membrane from one of the states to the other state.

In a further embodiment, the switching means may be designed to apply an electric and/or (e.g. constant) magnetic field to the membrane, for switching the membrane from one of the states to the other state.

In a further embodiment, the switching means may be designed to change the pH-value of a medium contacting said membrane for switching the membrane from one of the states to the other state.

In a further embodiment, the switching means may be designed to change the temperature of the membrane in order to switch the membrane from one of the states to the other state.

In yet another embodiment, the switching means may be designed to exert a pressure and/or a shear stress on said membrane in order to switch the membrane from one of the states to the other state.

According to a preferred embodiment, said switching means comprises a light source that is designed to illuminate said membrane, wherein the light source is particularly designed to illuminate the membrane with light comprising a first wavelength for switching the membrane into the first state, and wherein the light source is particularly designed to illuminate the membrane with light comprising a second wavelength different from the first wavelength for switching the membrane into the second state.

Preferably, the switching means comprises a light guide for guiding said light of the light source towards the membrane, so that the membrane can be irradiated with the respective light for switching it from one state to the other state.

Preferably, for receiving the said analyte diffusing from or to the skin though said membrane, the probe head comprises a diffusion chamber adjacent to said membrane.

Further, preferably, the diffusion chamber comprises an inlet for feeding a perfusion medium into the diffusion chamber, as well as an outlet for discharging said perfusion medium out of the diffusion chamber, particularly so as to transport said analyte diffusing through said membrane out of the diffusion chamber.

For measuring the concentration of the analyte in the blood or tissue of the patient, the system preferably comprises an analyzing means according to an embodiment of the present invention, wherein said analyzing means is designed to measure a first concentration of the analyte diffused through the membrane (e.g. in a fluid perfusion medium) residing in the first state, and wherein said analyzing means is designed to measure a second concentration of the analyte diffused through the membrane residing in the second state (e.g. in a fluid perfusion medium), and wherein particularly the analyzing means is designed to measure the concentration of the analyte in the blood or tissue using said first and second concentration $C_{ml}$ and $C_{mh}$ of the analyte (e.g. in said perfusion medium).

According to a preferred embodiment of the present invention, the analyzing means is connected to said outlet of the diffusion chamber, so that said perfusion medium together with the respective permeate can be transported to the analyzing means.

Preferably, the device is designed to guide a perfusion medium through the diffusion chamber taking along the analyte diffusing through the membrane, such that the perfusion medium comprises the first concentration of the analyte when the analyte diffused through the membrane residing in the first state, and such that the perfusion medium comprises the second concentration of the analyte when the analyte diffused through the membrane residing in the second state.

It is to be noted that the analyte may diffuse through the skin of the animal or the human and then through the membrane into the perfusion medium. However, in case the perfusion medium contains a high enough concentration of the analyte, the analyte diffuses through the membrane towards the skin of the animal or the human.

In this way the concentration of the analyte in the perfusion medium also changes depending on the permeability of the membrane.

The perfusion medium then carries the analyte towards the analyzing means which is designed to measure the first and second concentration of the analyte.

In case two membranes with different permeability with respect to the analyte are employed, the probe head means comprises a first diffusion chamber adjacent to said membrane for receiving said analyte and a second diffusion chamber adjacent to said further membrane for receiving said analyte (different concentration). Preferably, the first diffusion chamber comprises an inlet for feeding a perfusion medium into the first diffusion chamber, as well as an outlet for discharging said perfusion medium out of the first diffusion chamber, particularly so as to transport said perfusion medium together with the analyte out of the first diffusion chamber. Further, preferably, the second diffusion chamber comprises an inlet for feeding a perfusion medium into the second diffusion chamber, as well as an outlet for discharging said perfusion medium out of the second diffusion chamber, particularly so as to transport said perfusion medium together with the analyte out of the second diffusion chamber.

Concerning the probe head, it is conceivable that said probe head is separated into a first probe head comprising said first diffusion chamber and said membrane, as well as a second probe head comprising said second diffusion chamber and said further membrane. However, the probe head may also be formed by a single probe head containing both membranes and diffusion chambers.

In case two membranes having different permeabilities with respect to the analyte are employed, the analyzing means is designed to measure a first concentration of the analyte diffused through the membrane (e.g. in a perfusion medium), as well as a second concentration of the analyte diffused through the further membrane (e.g. in a perfusion medium). Again, the analyzing means is preferably designed to measure the concentration of the analyte in the blood or tissue using said first and second concentration. Further, depending on the fluid perfusion medium (see above), the analyte may diffuse from the skin through the respective membrane into the respective diffusion chamber or from the respective diffusion chamber through the respective membrane towards the skin of the person.

In order to receive the perfusion medium containing the first or second analyte concentration, the analyzing means is connected to said outlets, so that said perfusion medium together with the analyte can be transported to the analyzing means.

Advantageously, said measured two concentrations allow to estimate the concentration of the analyte in the blood (or skin) of the person without further calibration. Thus, the device according to the invention allows a self-calibrating estimation of said concentration of the analyte.

This is achieved as follows. The passive diffusion of said analytes through the skin and the membrane (or said first and second membrane) is modeled by Fick's law:

$$C_{g,body} - C_{g,sensor} = F_g(R_g + R_m) \qquad (1),$$

where $C_{g,body}$ is the wanted blood analyte (e.g. glucose) concentration, $C_{g,sensors}$ the analyte concentration in the diffusion chamber (or in the first and the second diffusion chamber), $F_g$ the analyte flow through the skin and the membrane, $R_g$ the skin resistance to analyte diffusion, $R_m$ the membrane resistance to analyte diffusion which has two values, one for each state or one for the first membrane and the other one for the second membrane (cf. above). The unknowns are the blood analyte concentration $C_g$ and the skin resistance to analyte diffusion $R_g$. With measuring the concentration and the analyte diffusion flow for both states of said membrane (i.e. both resistances) of for the first and the second membrane, both the skin resistance and the blood analyte concentration can be determined.

Preferably, for keeping the concentration gradient high, and thus the analyte diffusion flow high, the diffusion chamber (or the two diffusion chambers) is flushed with a perfusion medium (also denoted as perfusate) in a microdialyis setup. Thus, once integrated over the flow streamline through the respective diffusion (or microdialysis) chamber, equation (1) becomes:

$$C_{g,sensor} = \left(1 - \exp\left[-\frac{A_m}{Q_d(R_g + R_m)}\right]\right) C_{g,body} \quad (2)$$

the term $$\left(1 - \exp\left[-\frac{A_m}{Q_d(R_g + R_m)}\right]\right) \quad (3)$$

is also called the dialysate extraction fraction, where $Q_d$ is the dialysate flow and $A_m$ the microdialysis or diffusion chamber area in contact with the membrane.

If $$Q_d \frac{R_g + R_m}{A_m} \gg \frac{1}{2},$$

the dialysate extraction fraction in (3) can be linearized. Then Eqn. (2) becomes:

$$C_{g,sensor} = \frac{A_m}{Q_d} \frac{1}{R_g + R_m} C_{g,body} \quad (4)$$

Then, with measuring the two concentrations $C_{ml}$ and $C_{mh}$ for two corresponding membrane states/permeabilities (or for the two membranes), where the index ml stands for low resistance (i.e. high permeability) and the index mh stands for high resistance (i.e. low permeability), or two membrane resistance values $R_{ml}$ and $R_{mh}$, one gets the blood glucose concentration, from (4) (with $C_{ml}=C_{g,sensor}$ ($R_m=R_{ml}$) and $C_{mh}=C_{g,sensor}$ ($R_m=R_{mh}$)):

$$C_{g,body} = \frac{Q_d}{A_m}(R_{mh} + R_{ml}) \frac{C_{ml} C_{mh}}{C_{ml} - C_{mh}} \quad (5)$$

Preferably, the following approximation is used:
$R_{ml} \ll R_{mh}$, $R_{mh} = R_g$, and
$R_G = 1,200,000$ scm$^{-1}$
$Q_d = 5$ µL min$^{-1}$
$A_m = 4$ cm$^2$
leading to $$C_{g,body} = Q_d R_g C_{ml} C_{mh}/(C_{ml} - C_{mh}). \quad (5')$$

Correspondingly, in an embodiment of the present invention, said analyzing means of the device according to the invention is preferably designed to determine the concentration of the blood of the analyte (here e.g. glucose) by using relation (5) or (5').

Once the skin resistance to analyte diffusion $R_g$ has been measured with the previous method, one measurement of the analyte concentration in the perfusion method, corresponding to only one state of the membrane, if said membrane is implemented with two or more states, is enough to determine the blood concentration $C_{g,body}$ of said analyte according to equation (2) or (4).

If needed said analyzing means might also employ equation (2) for two measurements $C_{ml}=C_{g,sensor}$ ($R_m=R_{ml}$) and $C_{mh}=C_{g,sensor}$ ($R_m=R_{mh}$)) for two corresponding different membranes or membrane states with a non-linear calibration algorithm.

The analyzing means may comprise a microfluidic chip for measuring said concentrations $C_{ml}$ and $C_{mh}$ with a fluorescence measurement as described in [1].

According to a further embodiment of the present invention, the analyzing means and/or said microfluidic chip are integrated into the probe head. Particularly, the microfluidic chip (or analyzing means) comprising the form of a plate or layer is arranged on top of the diffusion chamber (comprising the form of plate or layer, too) on a side facing away from the membrane. Further features of such an integrated device are described below with references to some Figures.

According to a further embodiment, the membrane and/or the further membrane comprises a photochromic compound or a moiety thereof.

A photochromic compound in the context of the present invention refers to a compound that exhibits at least two forms, wherein the at least two forms are able to undergo a reversible transformation from the one form into the other form induced by absorption of electromagnetic radiation, and the at least two forms have different absorption spectra. The transformation may include reactions such as covalent bond formation, covalent bond breaking, cis-trans isomerization, heterolytic ring-opening or ring-closing.

According to a further embodiment, said membrane and/or the further membrane are formed out of an e.g. porous polycarbonate, and said membrane and/or the further membrane further comprises a spirobenzopyran moiety or a spirooxazine moiety.

Particularly, the membrane and/or the further membrane comprise or consist of a first polymer comprising a spirobenzopyran moiety or a spirooxazine moiety. More particularly, the first polymer, particularly a porous polycarbonate, is grafted with a compound or a second polymer, wherein the compound or the second polymer comprises a spirobenzopyran moiety or spirooxazine moiety.

Preferably, said membrane and/or the further membrane comprise an amphiphilic network comprising a spirooxazine moiety or a spirobenzopyran moiety.

A spirobenzopyran moiety in the context of the present invention particularly refers to a compound that is characterized by formula 1

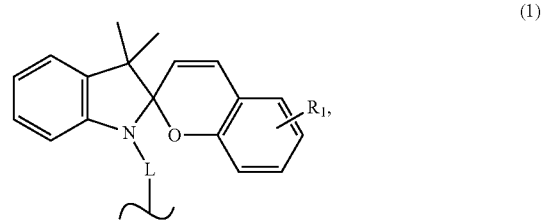

(1)

wherein

L is a linker, particularly a linker to the membrane and/or the further membrane or the first polymer, the compound or the second polymer, and wherein particularly the linker L comprises at least one methylene group (—CH$_2$—), and $R_1$ is selected from H and NO$_2$, A spirooxazine moiety in the context of the present invention particularly refers to compound that is characterized by formula 2a, 2b, 2c or 2d:

(2a)

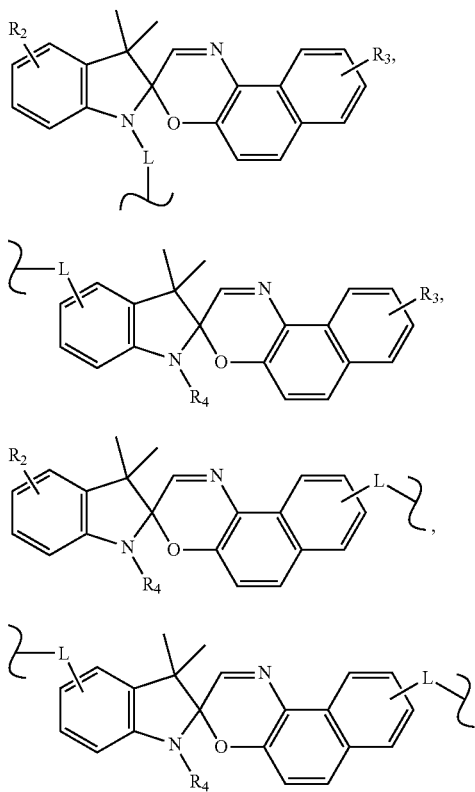

(2b)

(2c)

(2d)

wherein
L has the above meaning,
$L_1$ and $L_2$ are a linker, wherein particularly one of $L_1$ and $L_2$ is a linker to the membrane and/or the further membrane or the first polymer, the compound or the second polymer, and the other of $L_1$ and $L_2$ is a linker to an additional compound or polymer, wherein particularly the additional compound or polymer may comprise an additional a spirobenzopyran moiety or an additional spirooxazine moiety,
$R_2$ and $R_3$ are independently from each other selected from —O—C(O)—C(CH$_3$)=CH$_2$— and —O—C(O)—CH=CH$_2$, —NO$_2$, hydrogen or an alkyl, particularly CH$_3$, and
$R_4$ is hydrogen or an alkyl, particularly CH$_3$.

In some embodiments, the spirobenzopyran moiety is derived from a spirocompound characterized by formula 3:

(3)

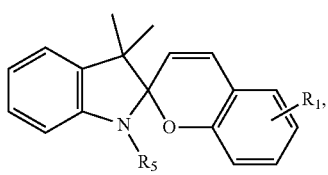

wherein
$R_1$ has the above meaning, and
$R_5$ is selected from —CH$_2$—CH$_2$—O—C(O)—CH=CH$_2$, —CH$_2$—CH$_2$—O—C(O)—C(CH$_3$)=CH$_2$, —CH$_2$—CH$_2$—C(O)—O—CH$_2$—CH$_2$—O—C(O)—CH=CH$_2$ and —CH$_2$—CH$_2$—C(O)—O—CH$_2$—CH$_2$—O—C(O)—C(CH$_3$)=CH$_2$.

In some embodiments, the spirooxazine moiety is derived from a spirocompound characterized by formula 4:

(4)

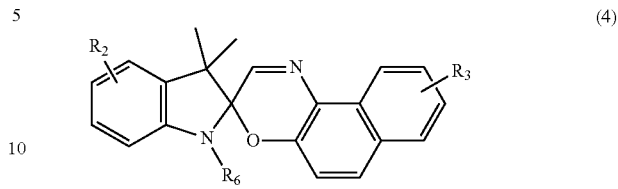

wherein
$R_2$ and $R_3$ are independently from each other selected from —O—C(O)—C(CH$_3$)=CH$_2$—, —O—C(O)—CH=CH$_2$, —NO$_2$, hydrogen and an alkyl, particularly CH$_3$, and
$R_6$ is selected from —CH$_2$—CH$_2$—O—C(O)—CH=CH$_2$, —CH$_2$—CH$_2$—O—C(O)—C(CH$_3$)=CH$_2$, —CH$_2$—CH$_2$—C(O)—O—CH$_2$—CH$_2$—O—C(O)—CH=CH$_2$, —CH$_2$—CH$_2$—C(O)—O—CH$_2$—CH$_2$—O—C(O)—C(CH$_3$)=CH$_2$, hydrogen and an alkyl, particularly CH$_3$,
provided that
at least one of $R_2$ and $R_3$ is —O—C(O)—C(CH$_3$)=CH$_2$— or —O—C(O)—CH=CH$_2$, or $R_6$ is —CH$_2$—CH$_2$—O—C(O)—CH=CH$_2$, —CH$_2$—CH$_2$—O—C(O)—C(CH$_3$)=CH$_2$, —CH$_2$—CH$_2$—C(O)—O—CH$_2$—CH$_2$—O—C(O)—CH=CH$_2$ or —CH$_2$—CH$_2$—C(O)—O—CH$_2$—CH$_2$—O—C(O)—C(CH$_3$)=CH$_2$.

In some embodiments, $R_6$ is hydrogen or an alkyl, particularly CH$_3$ and at least one of $R_2$ and $R_3$ is —O—C(O)—C(CH$_3$)=CH$_2$— or —O—C(O)—CH=CH$_2$.

In some embodiments, at least one of $R_2$ and $R_3$ is NO$_2$, hydrogen or an alkyl, particularly CH$_3$, and $R_6$ is —CH$_2$—CH$_2$—O—C(O)—CH=CH$_2$, —CH$_2$—CH$_2$—O—C(O)—C(CH$_3$)=CH$_2$, —OH$_2$—OH$_2$—C(O)—O—CH$_2$—CH$_2$—O—C(O)—CH=CH$_2$ or —CH$_2$—CH$_2$—C(O)—O—CH$_2$—CH$_2$—O—C(O)—C(CH$_3$)=CH$_2$ In some embodiments, the spirobenzopyran moiety is derived from a spirocompound selected from SP5 (2-(3',3'-dimethyl-6-nitro-spiro[chromene-2,2'-indoline]-1'-yl)ethanol), (2-(3',3'-dimethyl-6-nitro-spiro[chromene-2,2'-indoline]-1'-yl)ethyl 2-methylprop-2-enoate), (2-(3',3'-dimethyl-6-nitro-spiro[chromene-2,2'-indoline]-1'-yl)ethyl prop-2-enoate), SP12 (3-(3',3'-dimethyl-6-nitro-spiro[chromene-2,2'-indoline]-1-yl)propanoic acid), SP14 (2-[3-(3',3'-dimethyl-6-nitro-spiro[chromene-2,2'-indoline]-1'-yl)propanoyloxy]ethyl 2-methylprop-2-enoate) and SP16 (2-prop-2-enoyloxyethyl 3-(3',3'-dimethyl-6-nitro-spiro[chromene-2,2'-indoline]-1'-yl)propanoate).

In some embodiments, the spirooxazine moiety is derived from a spirocompound selected from SO37 (1',3',3'-trimethylspiro[benzo[f][1,4]benzoxazine-3,2'-indoline]-9-01), SO39 (1,3',3'-trimethylspiro[benzo[f][1,4]benzoxazine-3,2'-indoline]-9-yl) 2-methylprop-2-enoate), SO50 ((1',3',3'-trimethylspiro[benzo[f][1,4]benzoxazine-3,2'-indoline]-9-yl) prop-2-enoate) and SO49 ((5'-acetoxy-1',3',3'-trimethylspiro[benzo[f][1,4]benzoxazine-3,2'-indoline]-9-yl) prop-2-enoate).

Further, the problem according to the invention is solved by a method according to claim 18 for measuring the concentration of an analyte in the blood or tissue of an animal or a human, particularly a premature infant, wherein for measuring said concentration, and particularly the skin resistance of said animal or said human, the analyte is let to diffuse through a means comprising a first permeability with respect to said analyte as well as through a means comprising a second permeability with respect to said analyte, wherein said two permeabilities differ. Said means may comprise a single membrane comprising a first state in which the membrane comprises the first permeability and a second state in which the membrane comprises the second permeability. Alternatively said means may be formed by a membrane comprising (e.g. permanently) the first permeability as well as another further membrane comprising (e.g. permanently) said second permeability.

In a preferred embodiment the method comprises the steps of
- letting the analyte (that e.g. passively diffused through the skin of said animal or said human) diffuse through a membrane comprising a first permeability with respect to said analyte,
- letting the analyte (that e.g. passively diffused through the skin of said animal or said human) diffuse through a further membrane or through said membrane comprising a second permeability with respect to said analyte, and
- measuring a first concentration of the analyte diffusing through the membrane comprising the first permeability and a second concentration of the analyte diffusing through the membrane comprising the second permeability or through the further membrane comprising the second permeability,
- and determining the concentration of said analyte in the blood or tissue using said first and second concentration.

Preferably, the device according to the invention is used for conducting the method according to the invention.

Preferably, when a membrane having two states (each with a different permeability concerning the analyte) is used, the membrane is brought to its first state.

Preferably, the analyte (that e.g. passively diffused through the skin of the patient) is let to diffuse through the membrane residing in the first state and is then preferably collected in the diffusion chamber, preferably in a perfusion medium. Alternatively the analyte may diffuse from the diffusion chamber (e.g. out of the perfusion medium) through the membrane in the first state towards the skin (here also a specific first concentration of the analyte is established in the perfusion medium which in this case contains the analyte right from the start, see above). The first permeability may be higher than the second one (or vice versa).

Preferably, the perfusion medium with the first concentration of the analyte is transported to the analyzing means, particularly by pumping the perfusion medium through the diffusion chamber which takes along the analyte to the analyzing means.

Preferably, the first concentration of the analyte in the fluid perfusion medium is measured and particularly stored by the analyzing means.

Preferably, the membrane is then switched from the first state to the second state, particularly by irradiating light of a first wavelength on the membrane so as to keep it in the first state, and then by irradiating the membrane with light of a second wavelength in order to switch and keep it in the second state. Any other method described above may also be used.

Then, preferably, the analyte (that e.g. passively diffused through the skin of the patient) is let to diffuse through the membrane residing in the second state and is then preferably collected in the diffusion chamber, preferably in a perfusion medium. Alternatively, the analyte may diffuse from the diffusion chamber (e.g. out of the perfusion medium) through the membrane in the second state towards the skin (here also a specific second concentration of the analyte is established in the perfusion medium which in this case again contains the analyte right from the start, see also above).

Preferably, the perfusion medium showing the second concentration of the analyte (being lower or higher than the first concentration before) is transported to the analyzing means, particularly by pumping the perfusion medium through the diffusion chamber which takes along the analyte to the analyzing means.

Preferably, the second concentration of the analyte in the perfusion medium is measured.

Preferably, the concentration of the analyte in the blood (e.g. glucose) or skin is then determined by the analyzing means using the two measured concentrations, e.g. as described above by using relations (5) or (5').

The analyzing means may comprise a computer on which a suitable computer program is executed comprising program code that is adapted for determining the concentration of the analyte in the blood or tissue of the person using the two measured concentrations, e.g., said relations (5) or (5') described above.

In case a (first) membrane and a further (second) membrane are used, the method is preferably carried out as follows:

Preferably, the analyte (that e.g. passively diffused through the skin of the patient) is collected in the first diffusion chamber of the probe head via the first membrane (e.g. in a perfusion medium) by contacting the skin with the first membrane so that said analyte diffuses through the first membrane. Alternatively, the analyte may diffuse from the first diffusion chamber (e.g. out of the perfusion medium) through the (first) membrane towards the skin (here also a specific first concentration of the analyte is established in the perfusion medium which in this case contains the analyte right from the start, see above). The first permeability may be higher than the second one (or vice versa).

Preferably, the perfusion medium showing the first concentration of the analyte is transported to the analyzing means, particularly by pumping the perfusion medium through the first diffusion chamber which takes along the analyte to the analyzing means.

Preferably, the (first) concentration of the analyte in the perfusion medium is measured and particularly stored by the analyzing means.

Then, preferably, the analyte (that e.g. passively diffused through the skin of the patient) is collected in the second diffusion chamber of the probe head via the second membrane (e.g. in a perfusion medium) by contacting the skin with the second membrane so that the analyte diffuses through the second membrane.

Collecting the analyte in the first and second diffusion chamber can in principle be done simultaneously, i.e. in parallel.

Preferably, the perfusion medium showing the second concentration of the analyte (being lower or higher than the first concentration) is transported to the analyzing means, particularly by pumping the perfusion medium through the second diffusion chamber which takes along the analyte to the analyzing means.

Preferably, the second concentration of the analyte in the fluid perfusion medium is measured. In principle, the two concentrations of the analyte may be measured simultaneously, i.e. in parallel.

Preferably, the concentration of the analyte in the blood (e.g. glucose) or skin is then determined by the analyzing means using the two measured concentrations, e.g. as described above by using relations (5) or (5').

Again, the analyzing means may comprise a computer on which a suitable computer program is executed comprising program code that is adapted for determining the concentration of the analyte in the blood or tissue of the person using the two measured concentrations, e.g., said relations (5) or (5') described above.

Advantageously, the method according to the invention is non-invasive for very permeable skin, as the one of preterm infants, or for measuring analytes to which the skin is very permeable (i.e. all molecules that go through the untreated skin in measurable amount, such as e.g. glucose for the preterm neonate). In this case, no invasive methods (e.g. microneedles) at all are necessary for measuring the blood analyte concentration.

However, the method according to the invention may also be used with lesser permeable skin. Here, prior to conducting the method according to the invention, the skin of the patient may be prepared with minimally invasive methods (e.g. microneedles puncturing the skin, skin abrasion, thinning of the stratum corneum by microdrilling with a laser array or other chemical, electromagnetic, thermal and mechanical methods) in order to make the skin sufficiently permeable for the desired analytes.

Further, the skin may be prepared in order to increase its permeability prior to measuring the desired analyte according to the invention by means of sonophoresis, electrophoresis, or by removing the superficial skin layers mechanically or chemically.

According to a further aspect of the present invention which may also be formulated as an independent claim, a device is provided, wherein the analyte is not diffusing through the skin of an animal or a human, but is diffusing passively through a barrier whose resistance to diffusion is unknown from a reservoir whose concentration is unknown and will be measured by the device.

Further features and advantages of the invention shall be described by means of a detailed description of embodiments with reference to the Figures, wherein FIG. 1 shows a schematical view (not to scale) of an embodiment of the device according to the invention;

Figure 16:
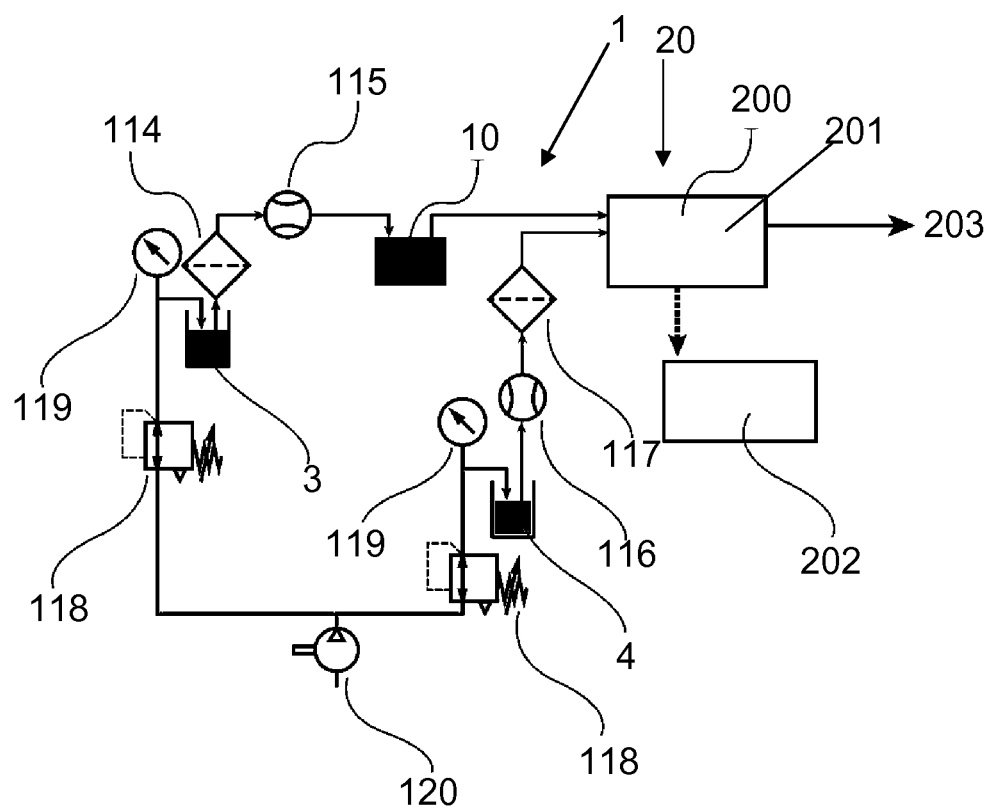
FIG. 16 shows a schematic overview of the device according to the invention.
Figure 17:
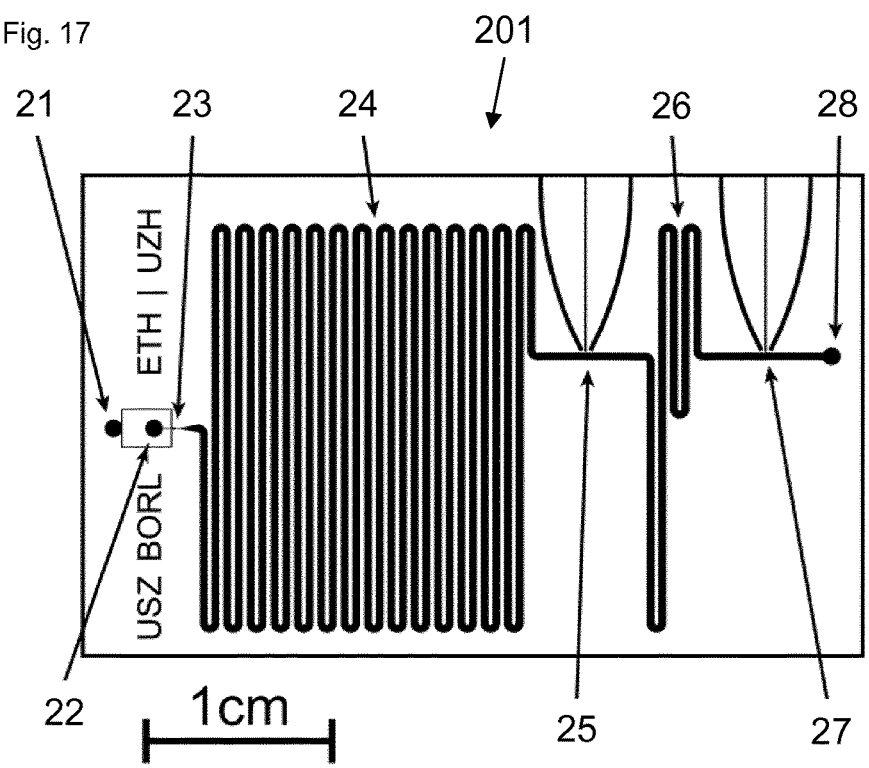
FIG. 17 shows a microfluidic chip of the device according to the invention for measuring glucose concentration.
Figure 28:
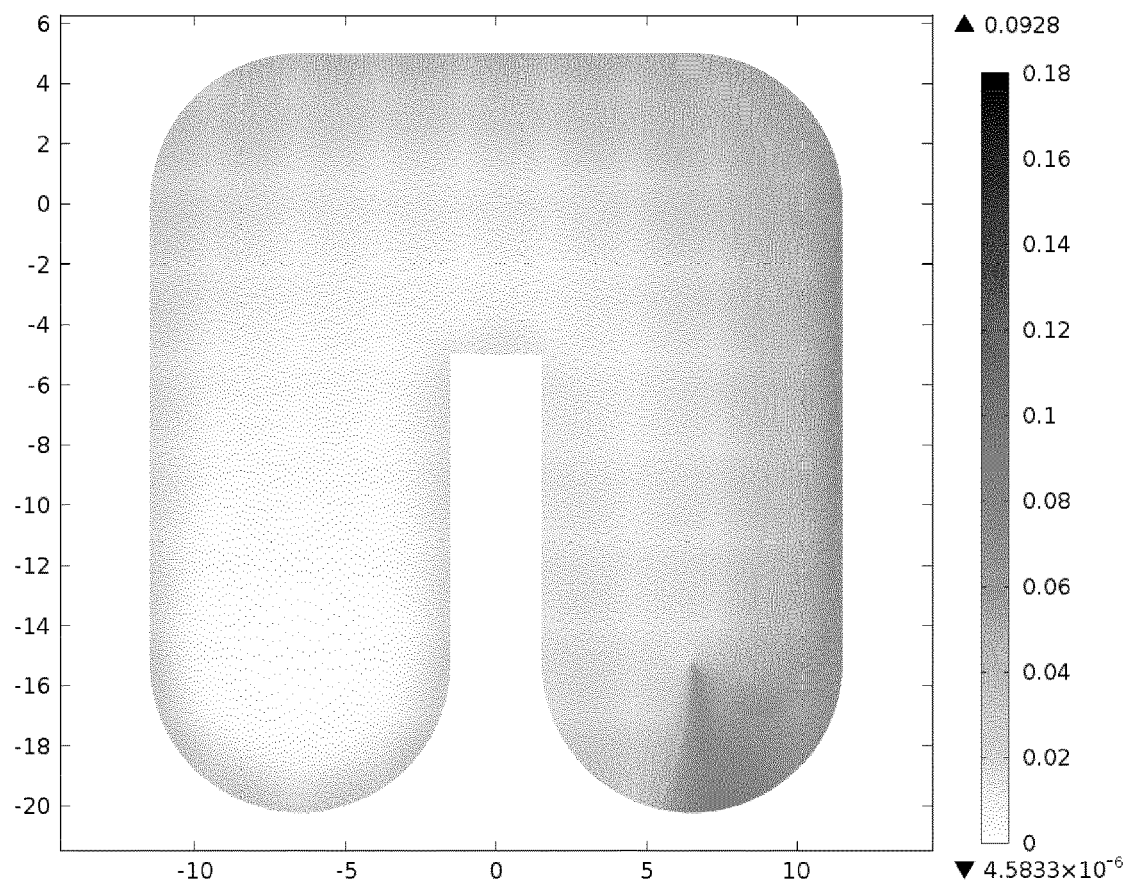
FIG. 28 shows a cross-section of the diffusion chamber showing the local dialysate extraction fraction having values between 0 (no substance extracted) and 1 (same concentration as in the blood). Shown are the results from a 3D Finite Element Method with a low permeability of the membrane.
Figure 29:
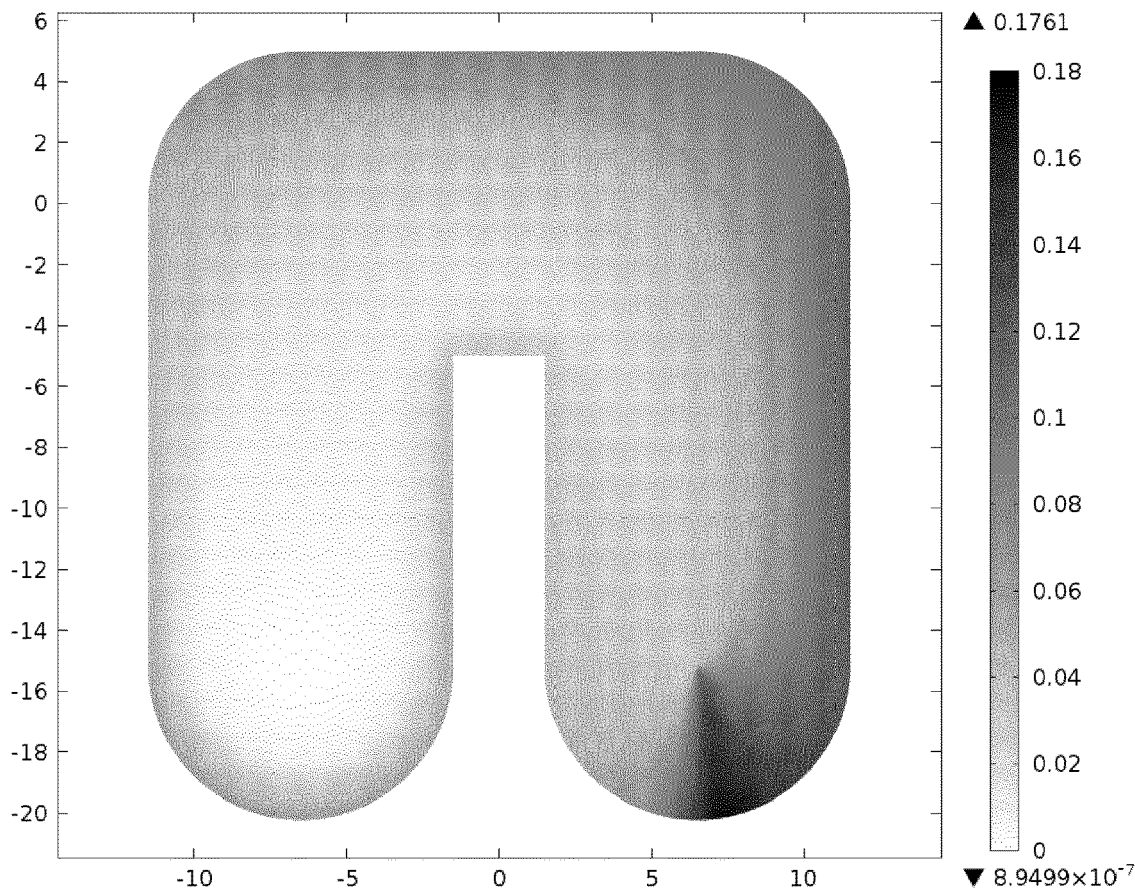
Figure 30:
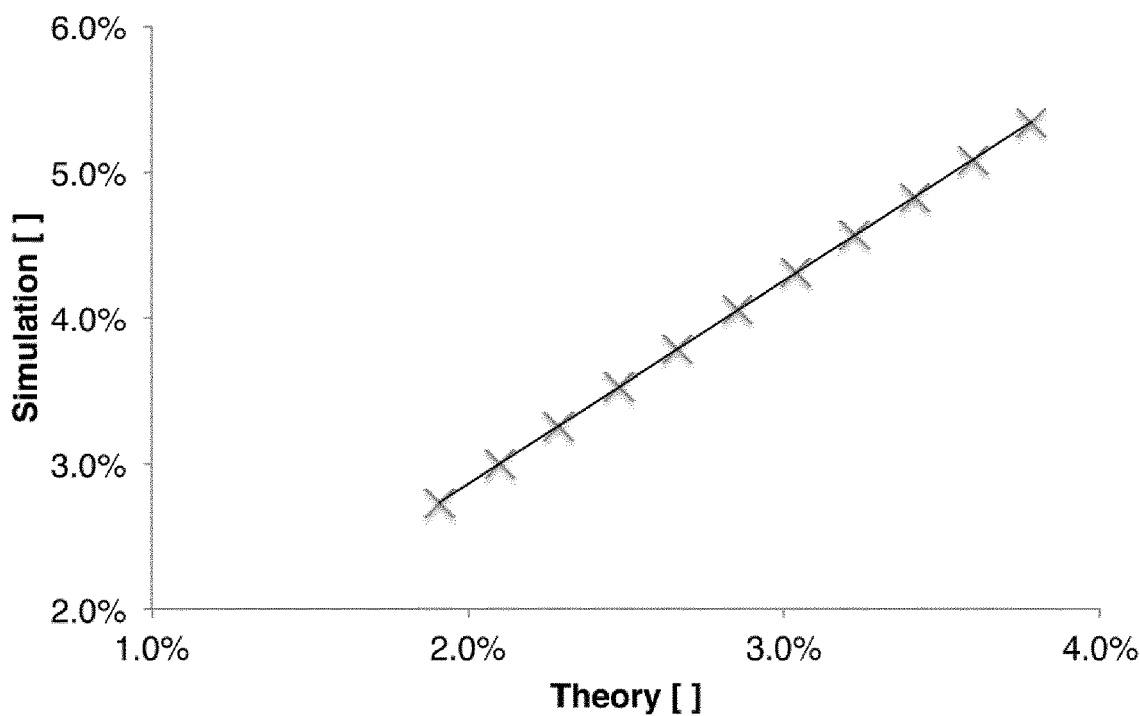
Figure 31:
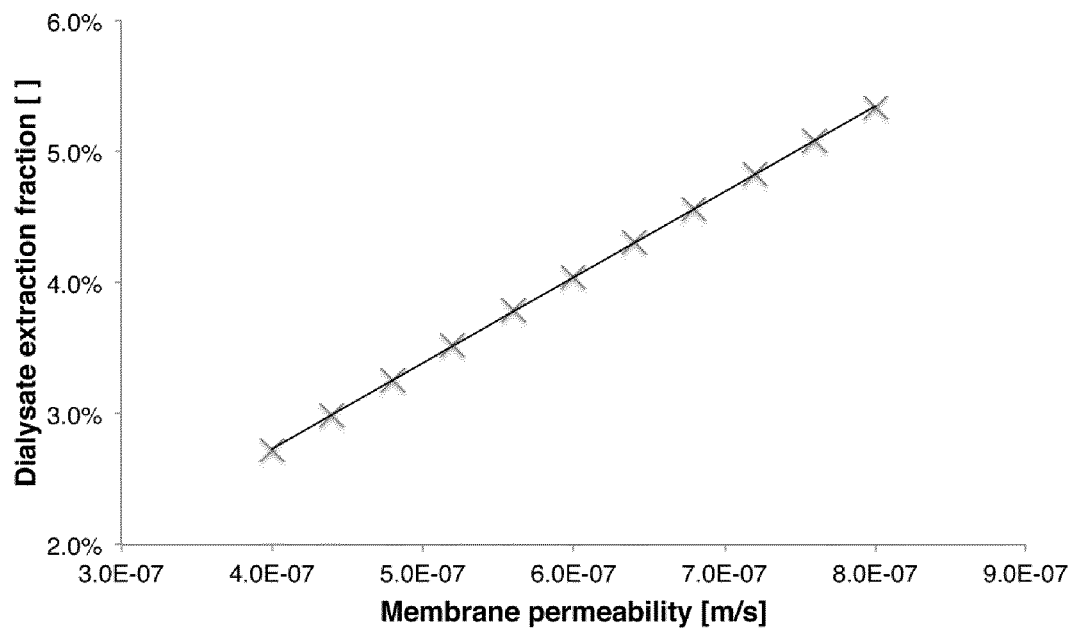
Figure 32:
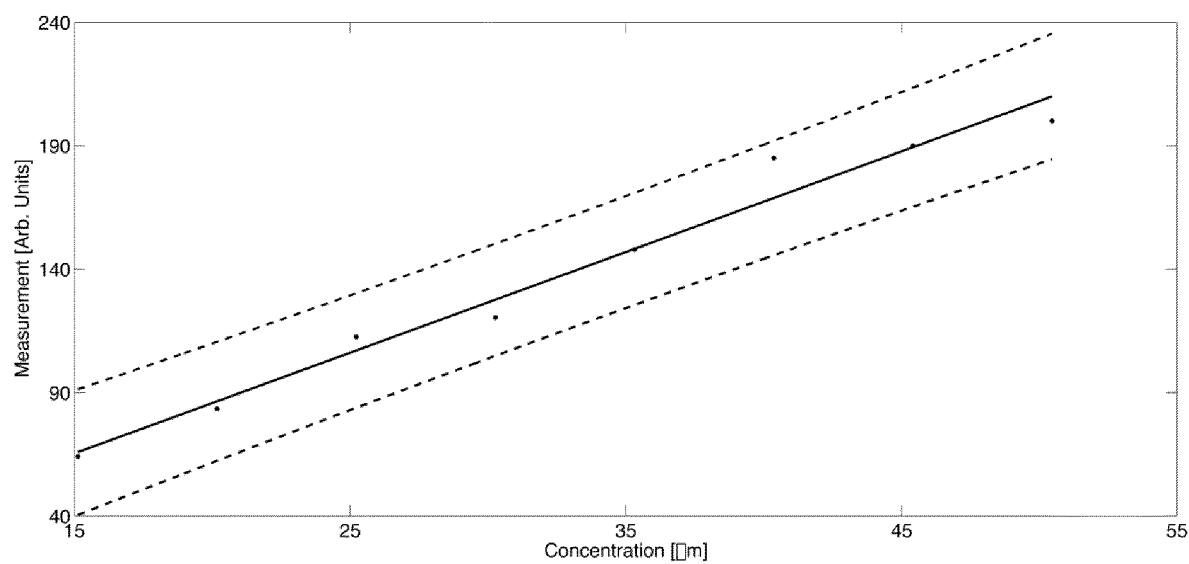
Figure 33:
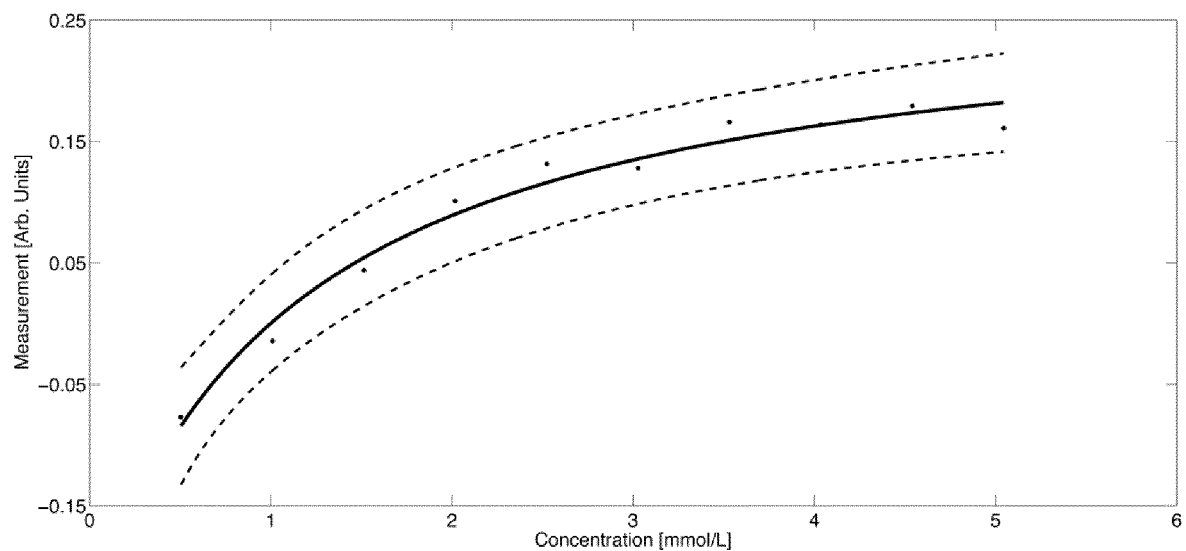
Figure 34:
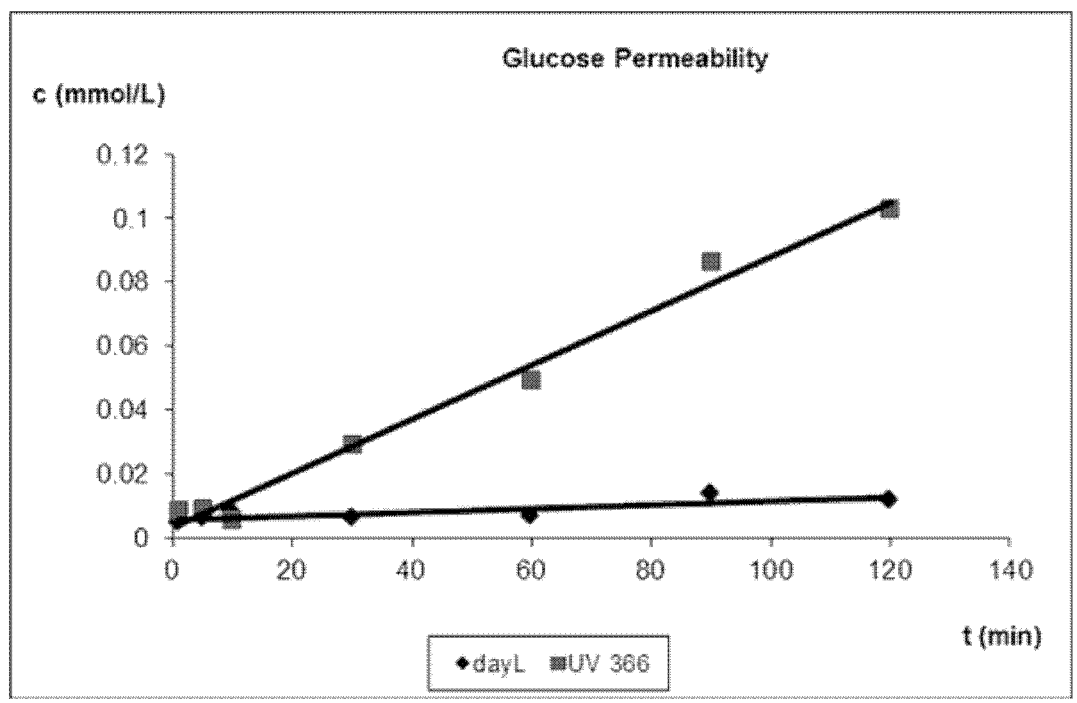
Figure 35:
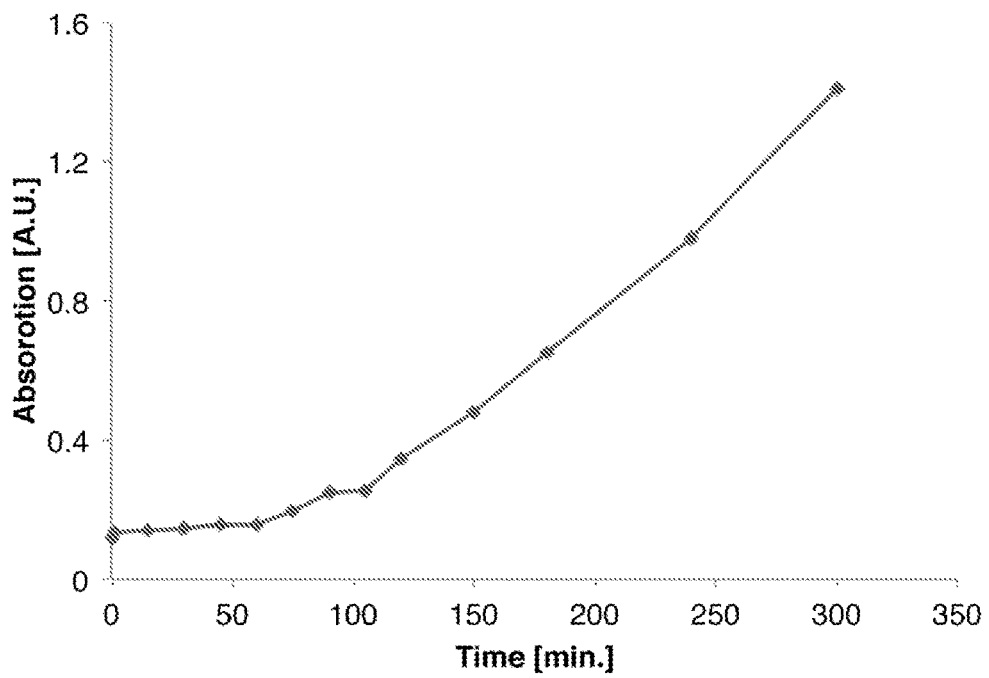
Figure 36:
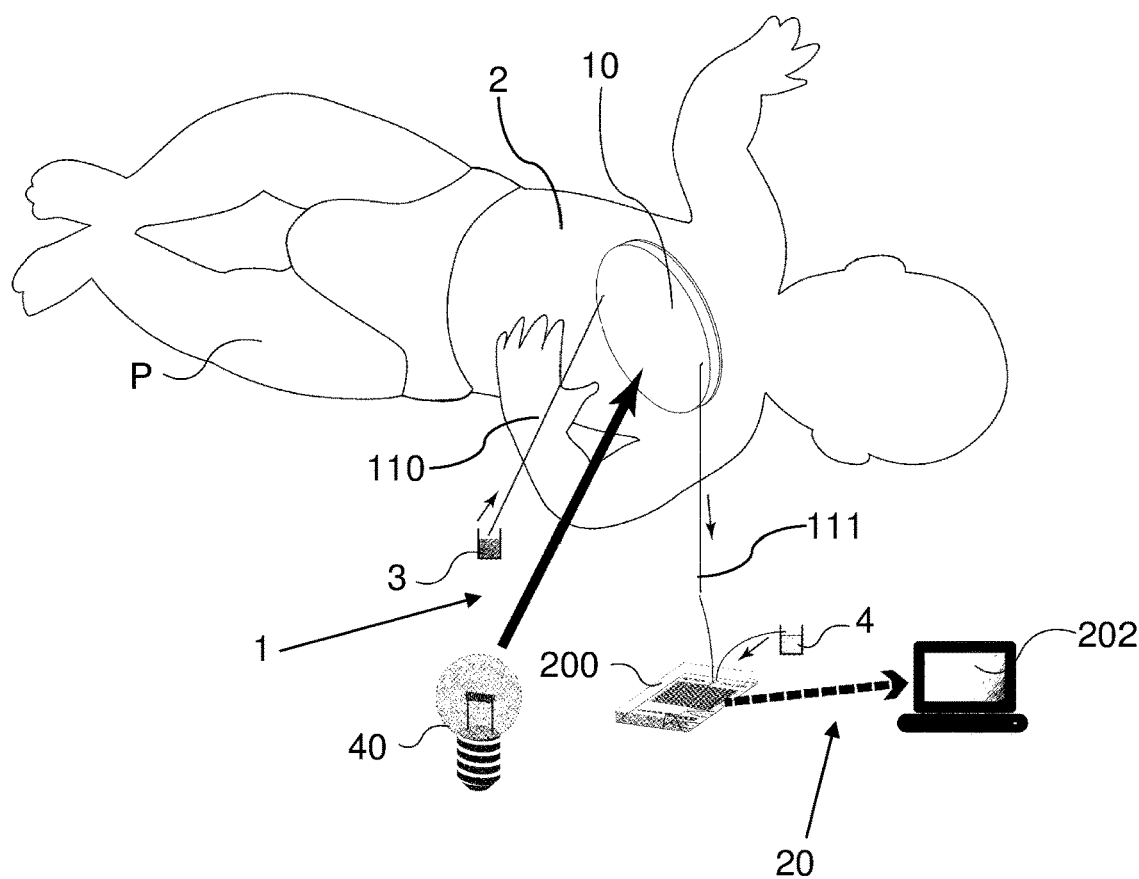
Figure 37:
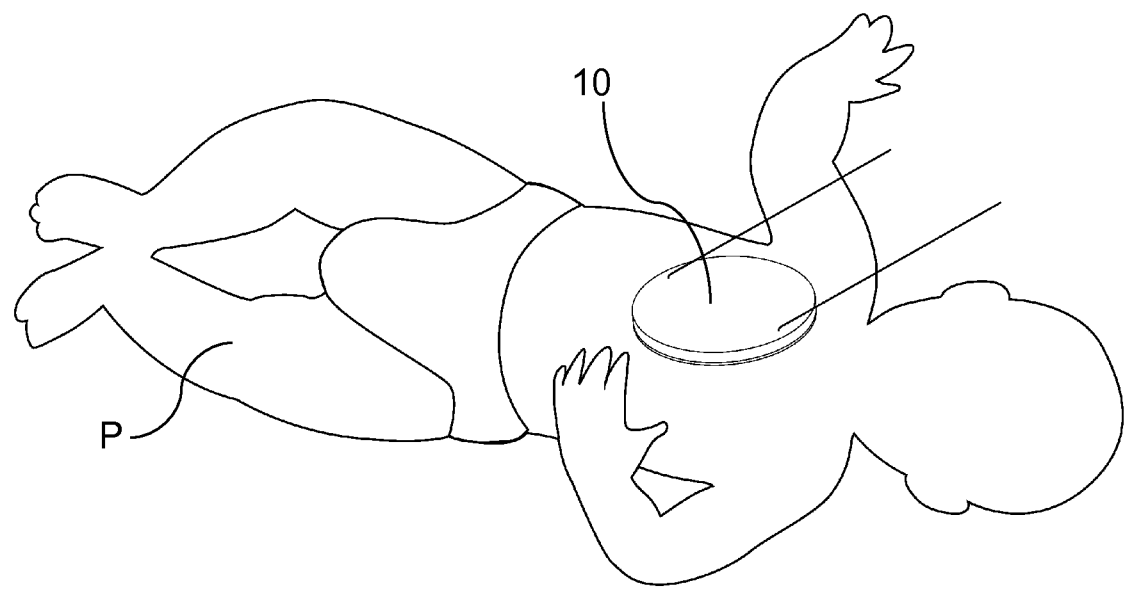
Figure 38:
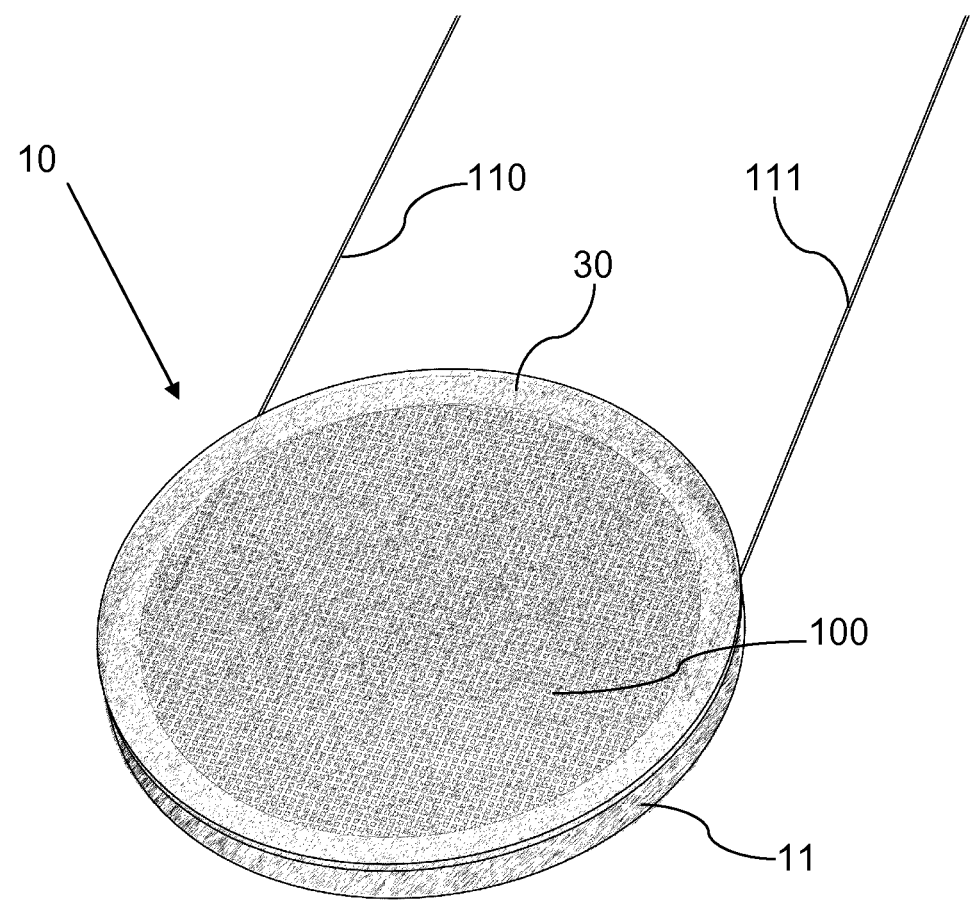
Figure 39:
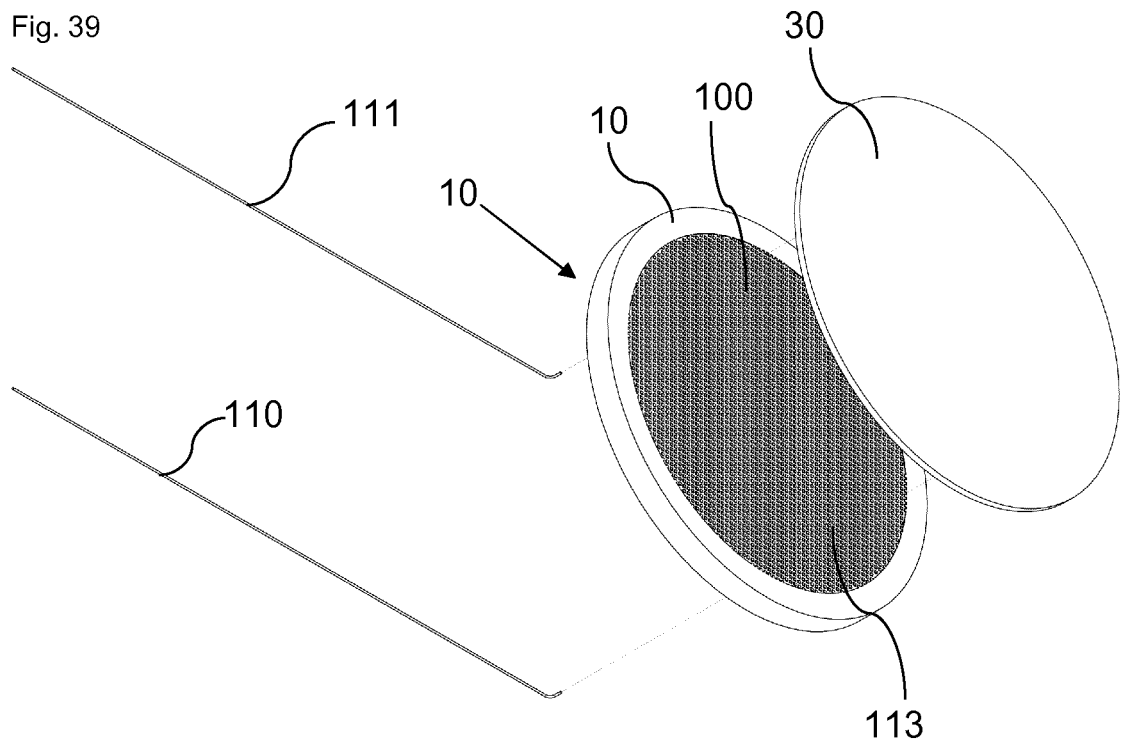
Figure 40:
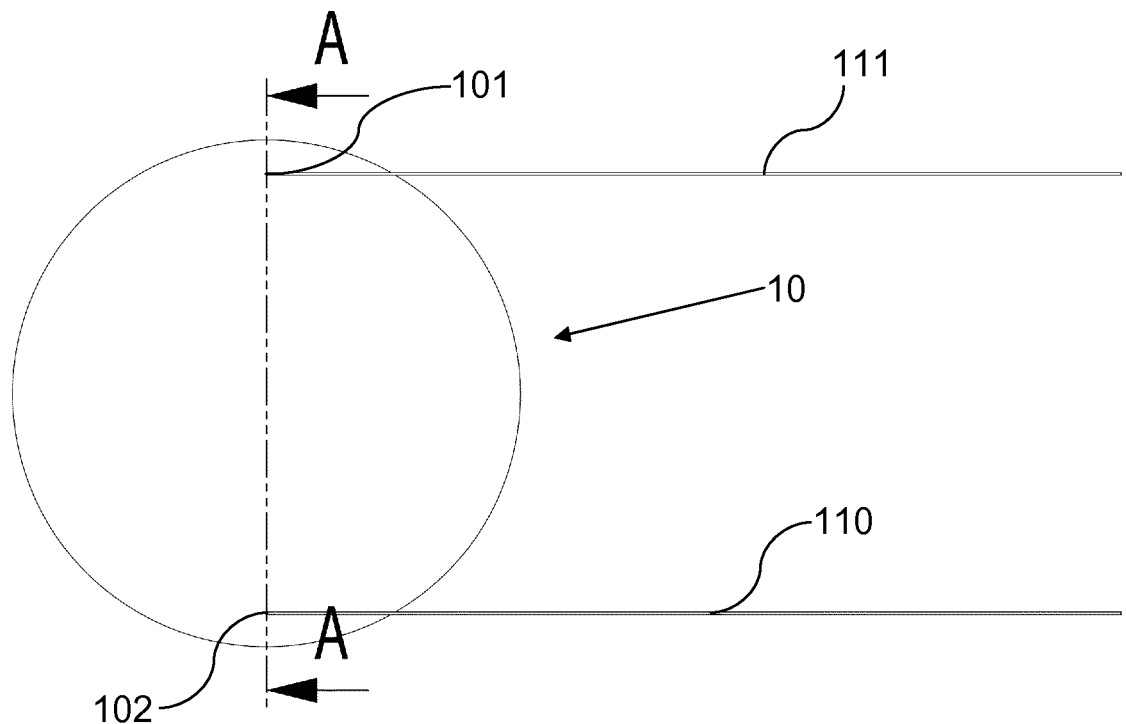
Figure 41:
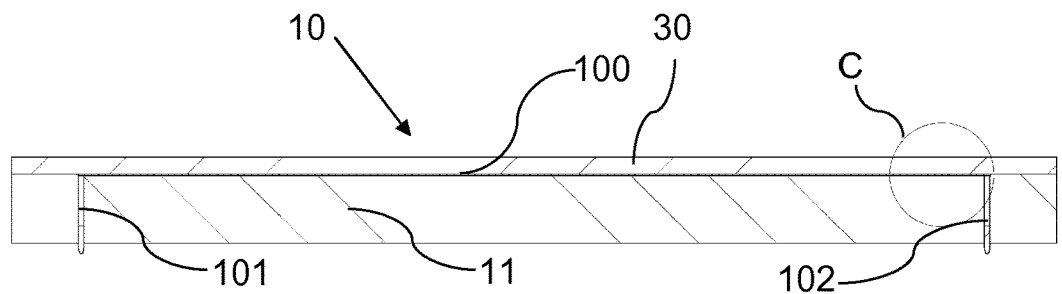
Figure 42:
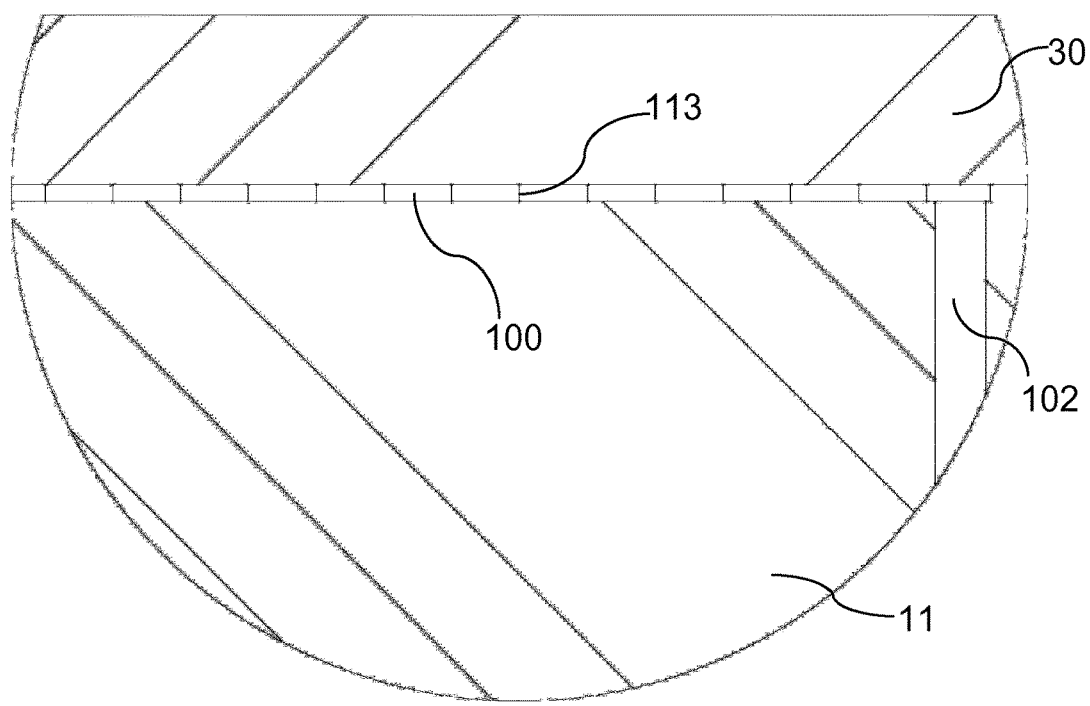
Figure 43:
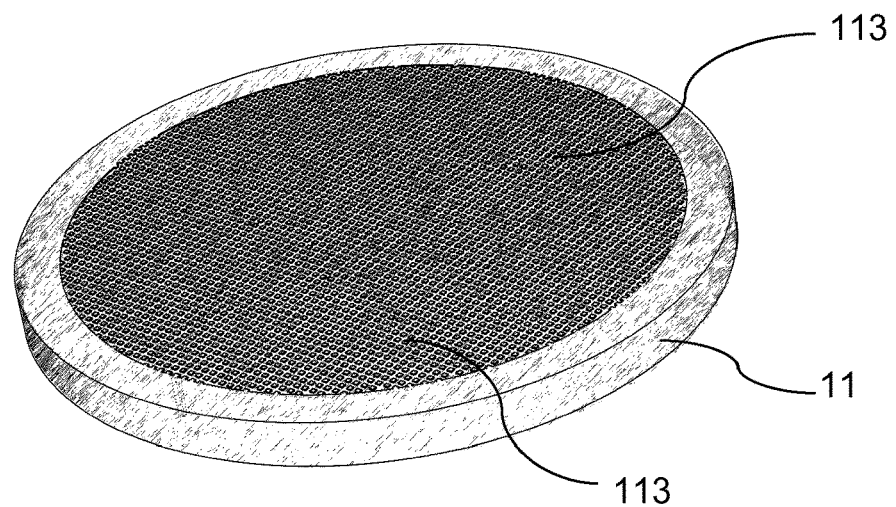
Figure 44:
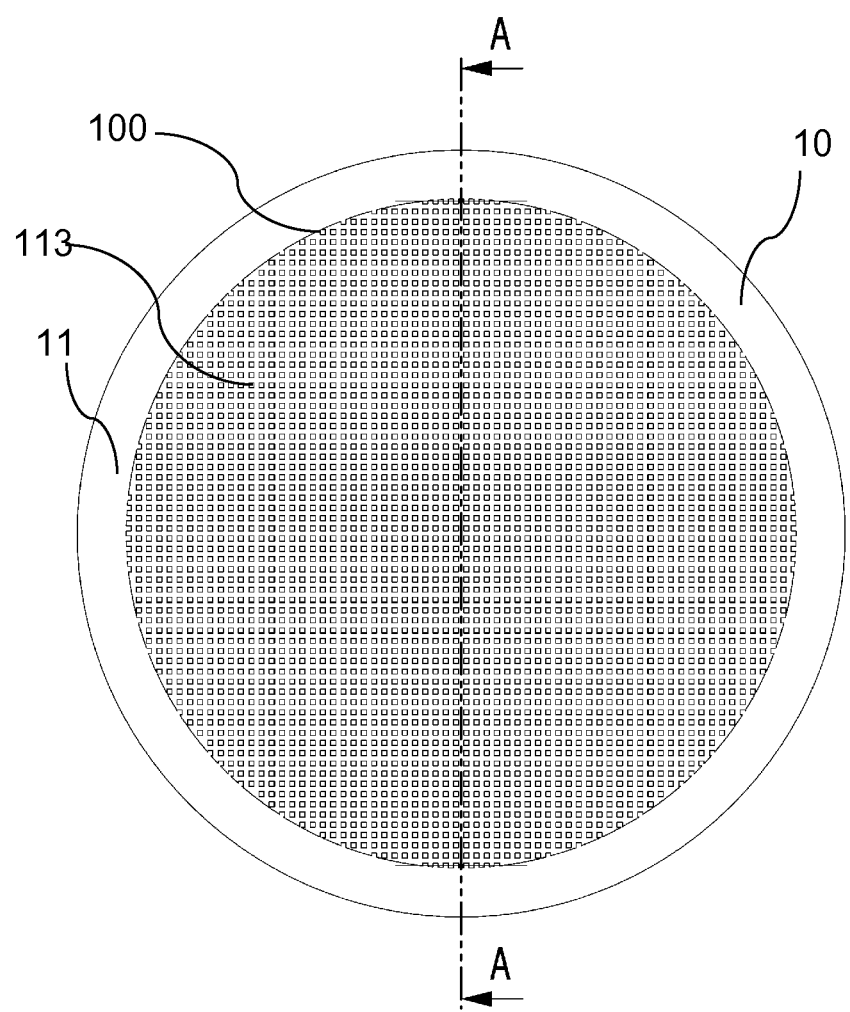
Figure 45:
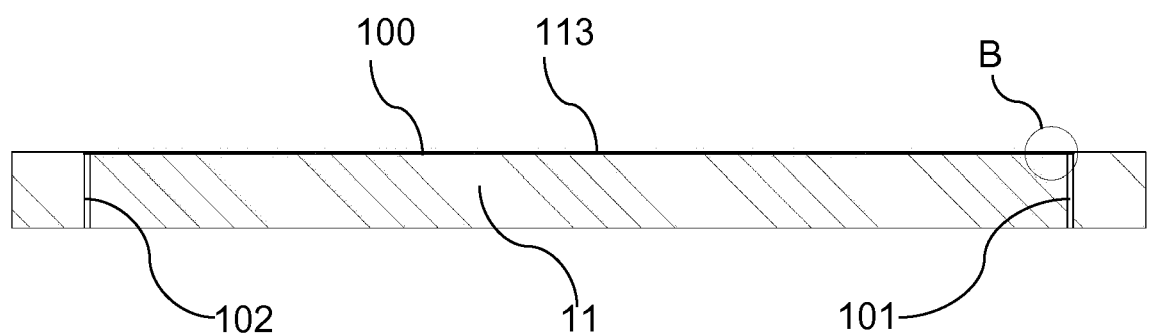
Figure 46:
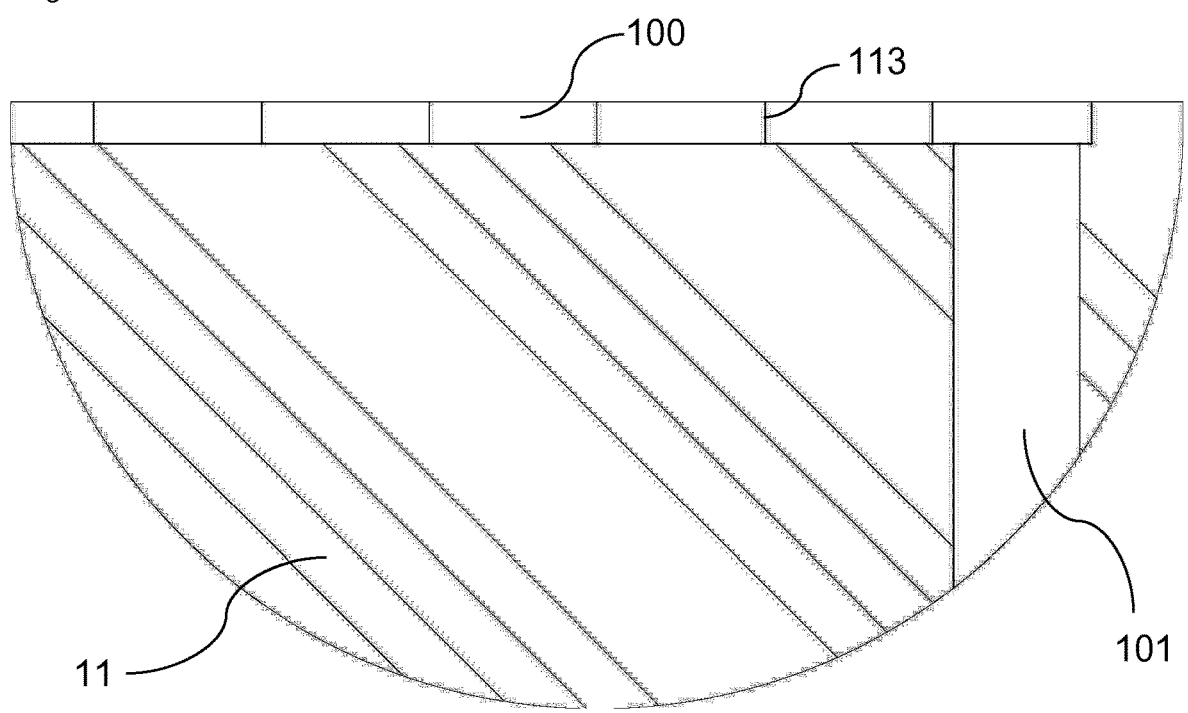
Figure 47:
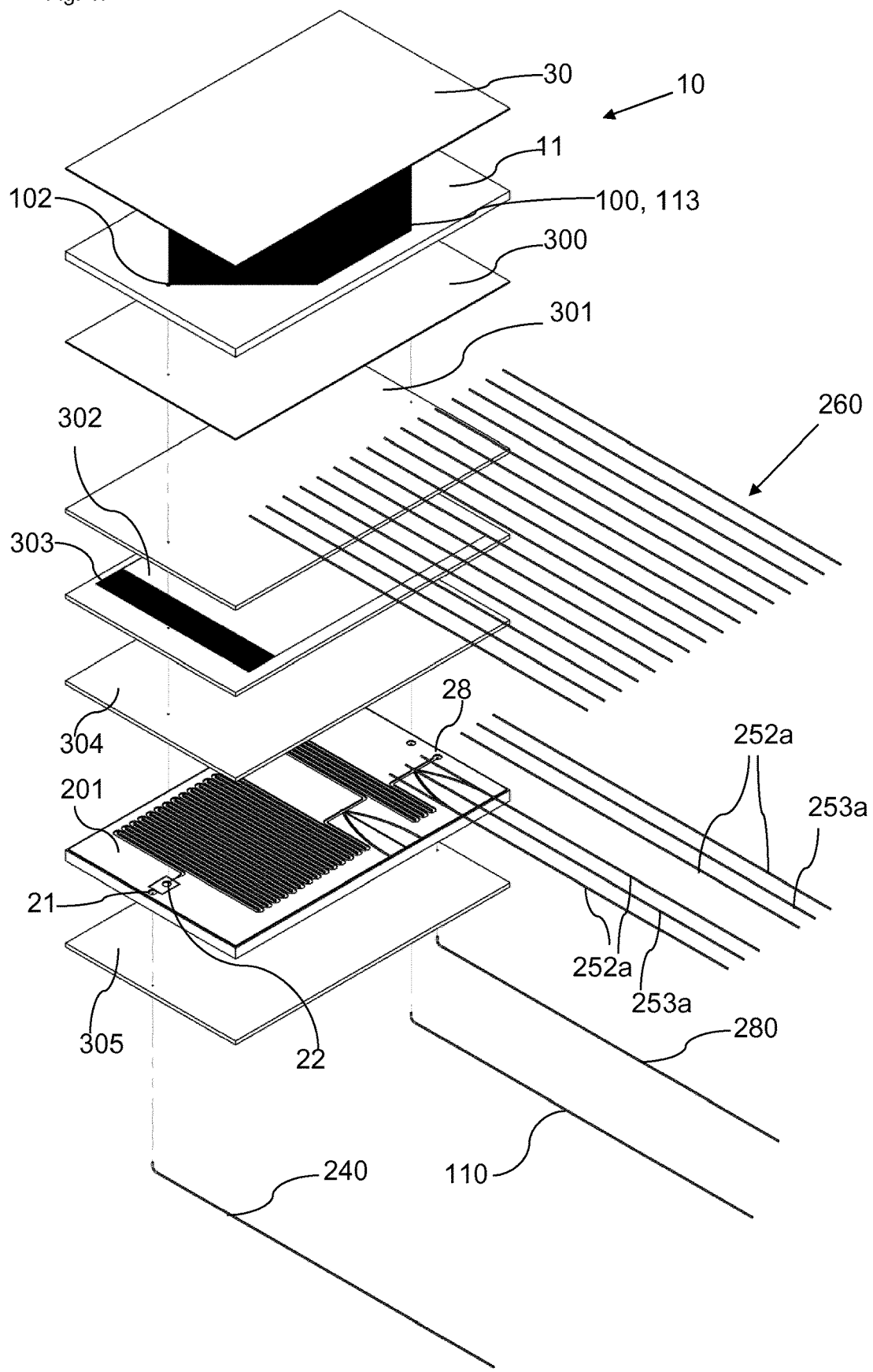
Figure 48:
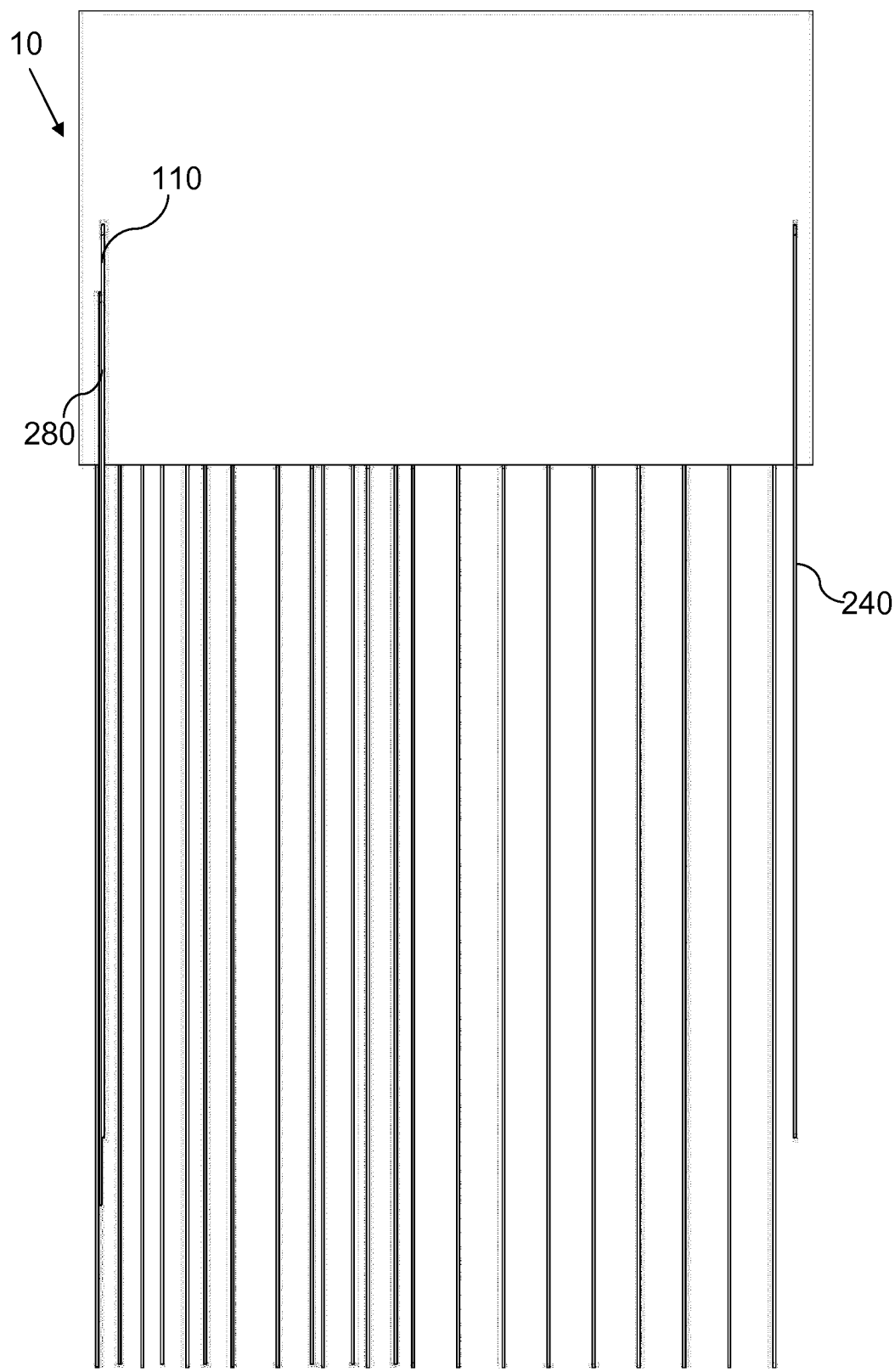
Figure 49:
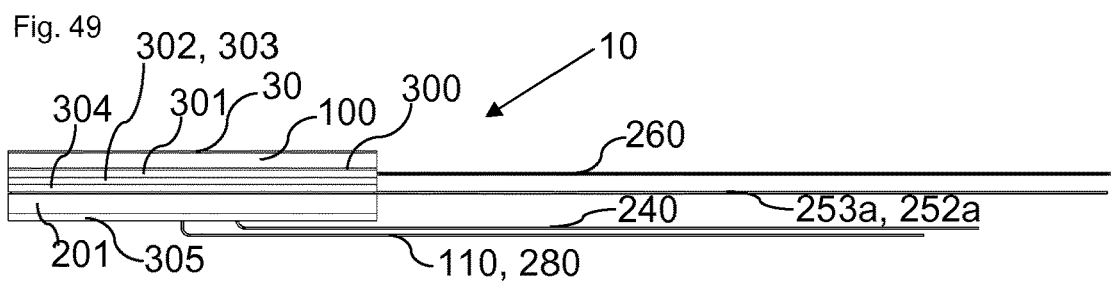
Figure 50:
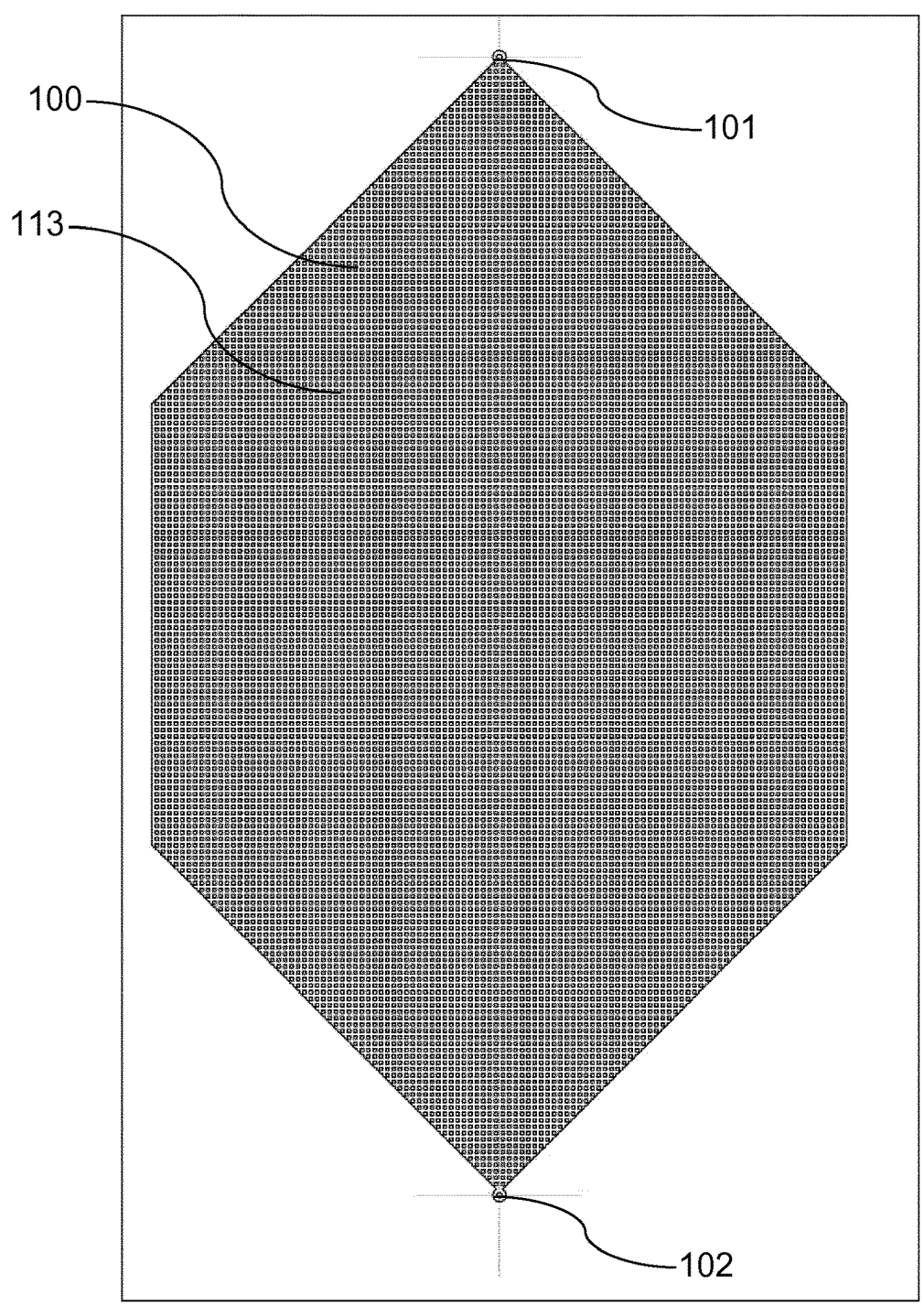
Figure 51:
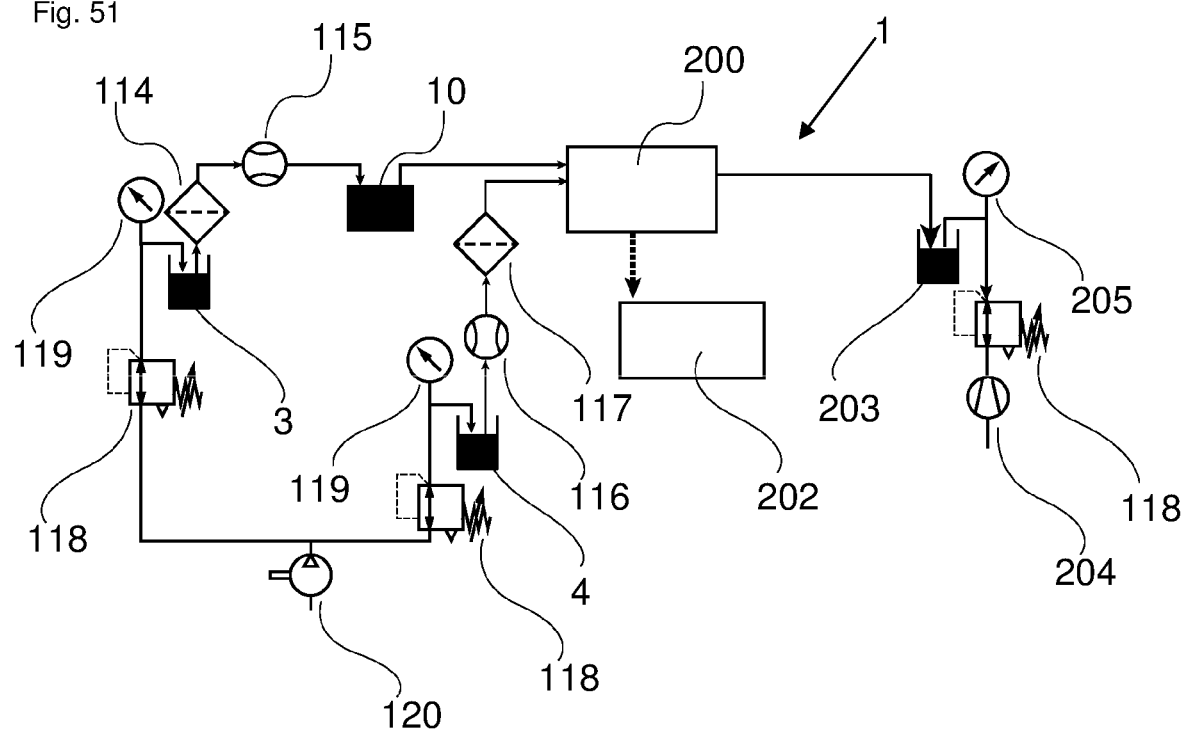
Figure 52:
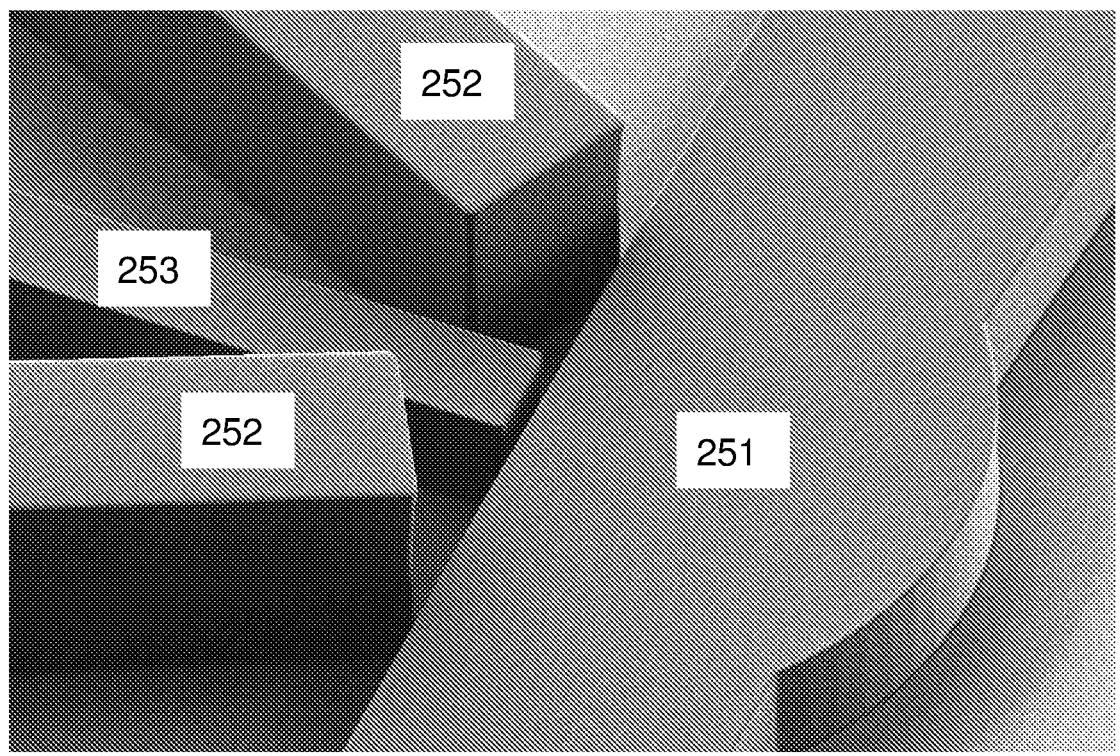
Figure 53:
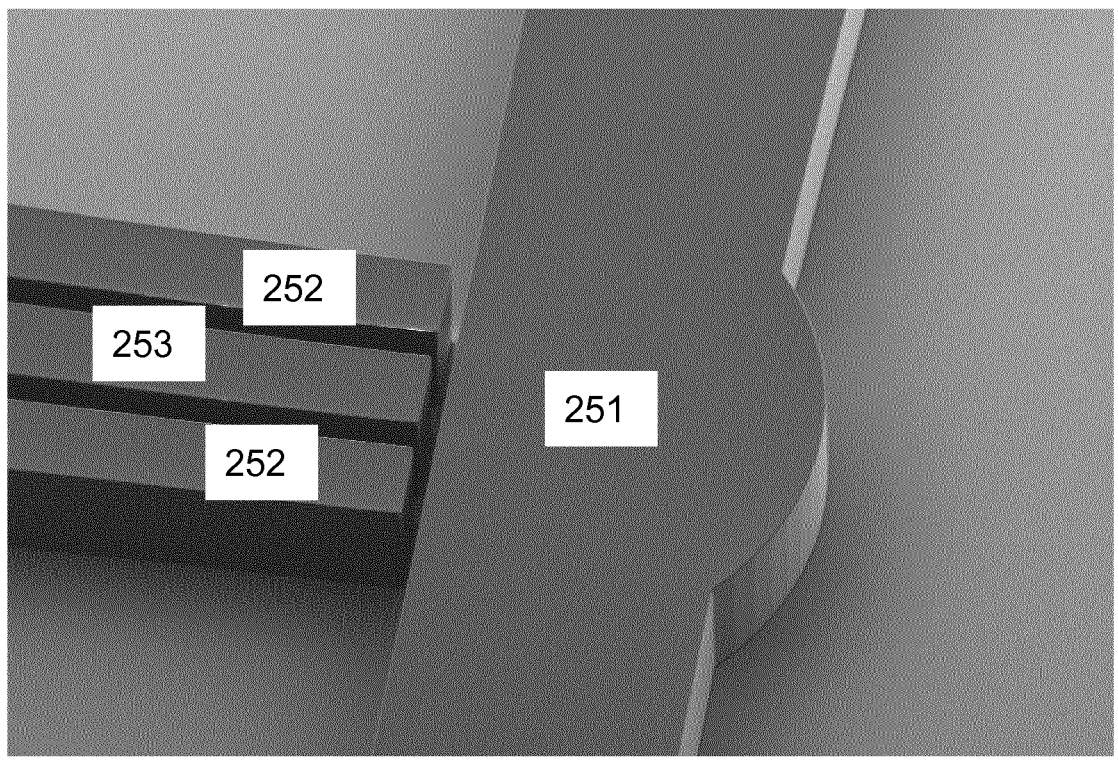
Figure 54:
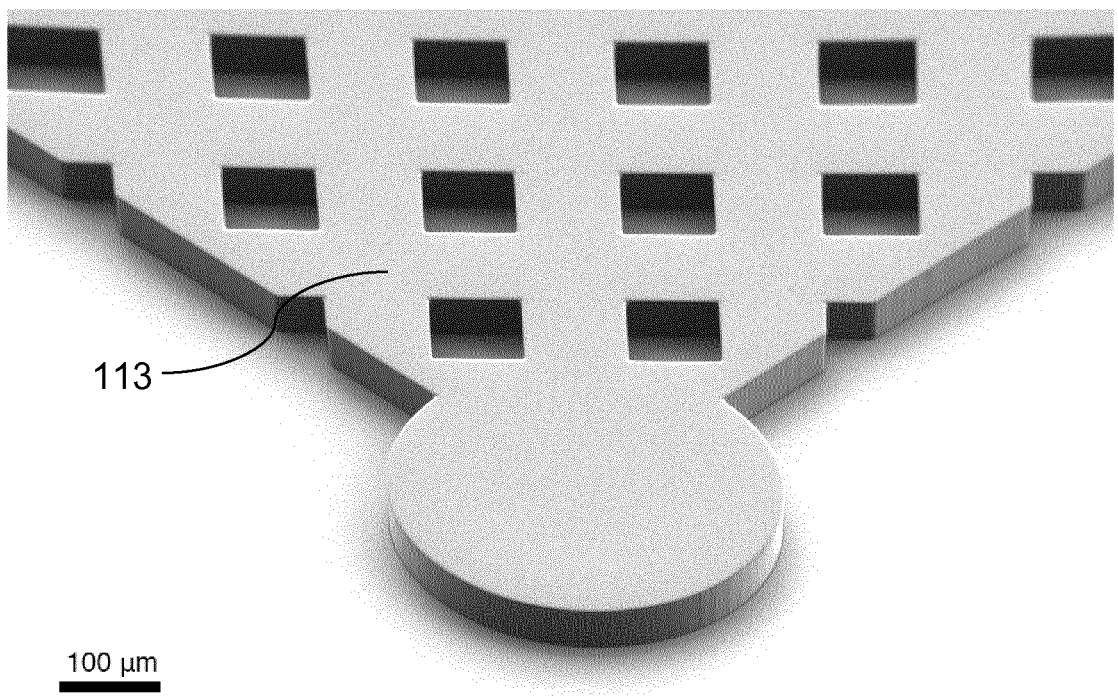
Figure 55:
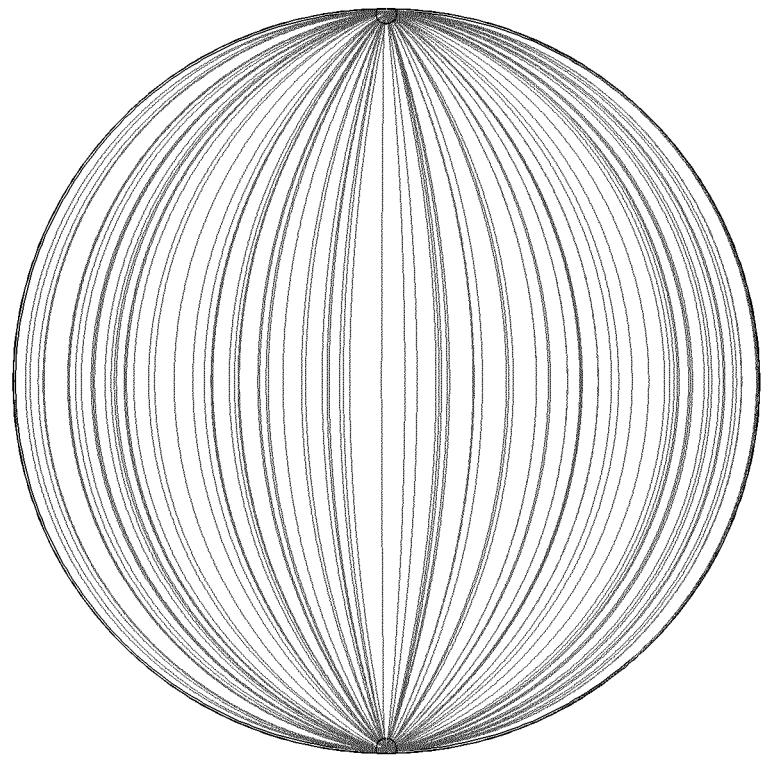
Figure 56:
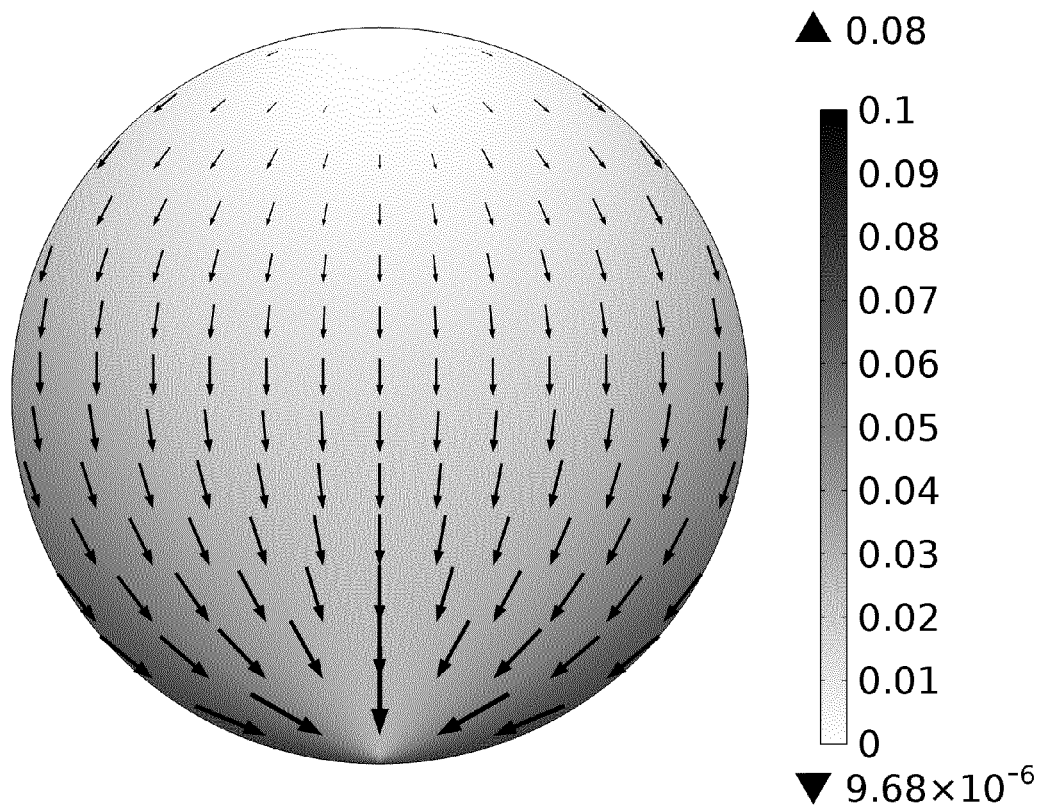
Figure 57:
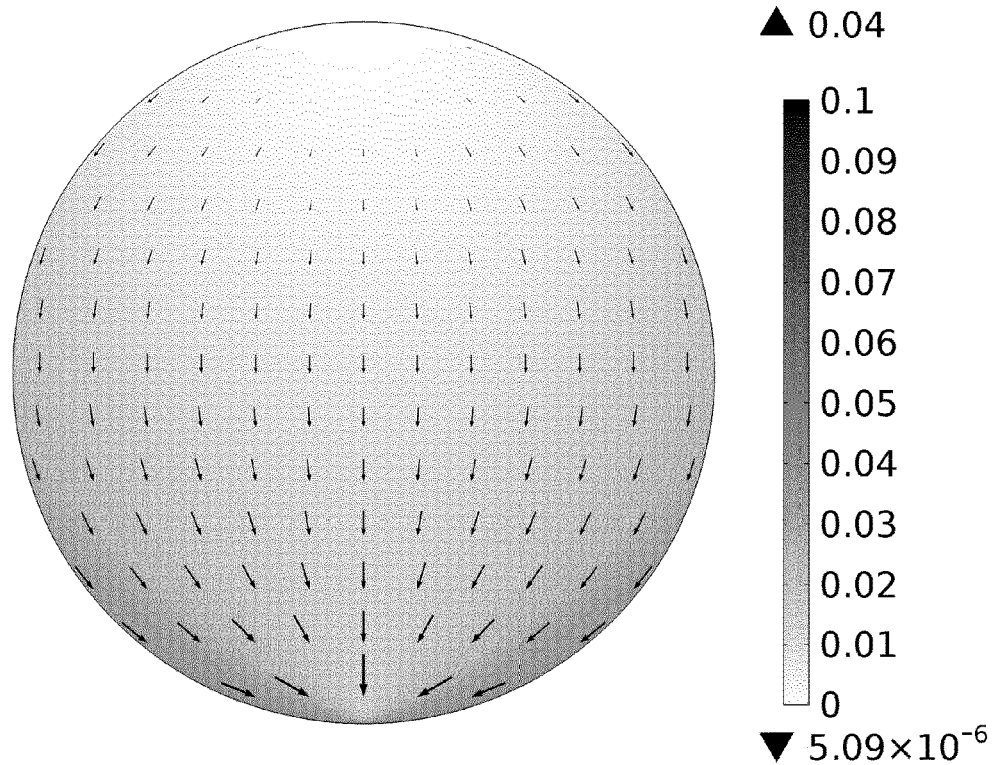
Figure 58:
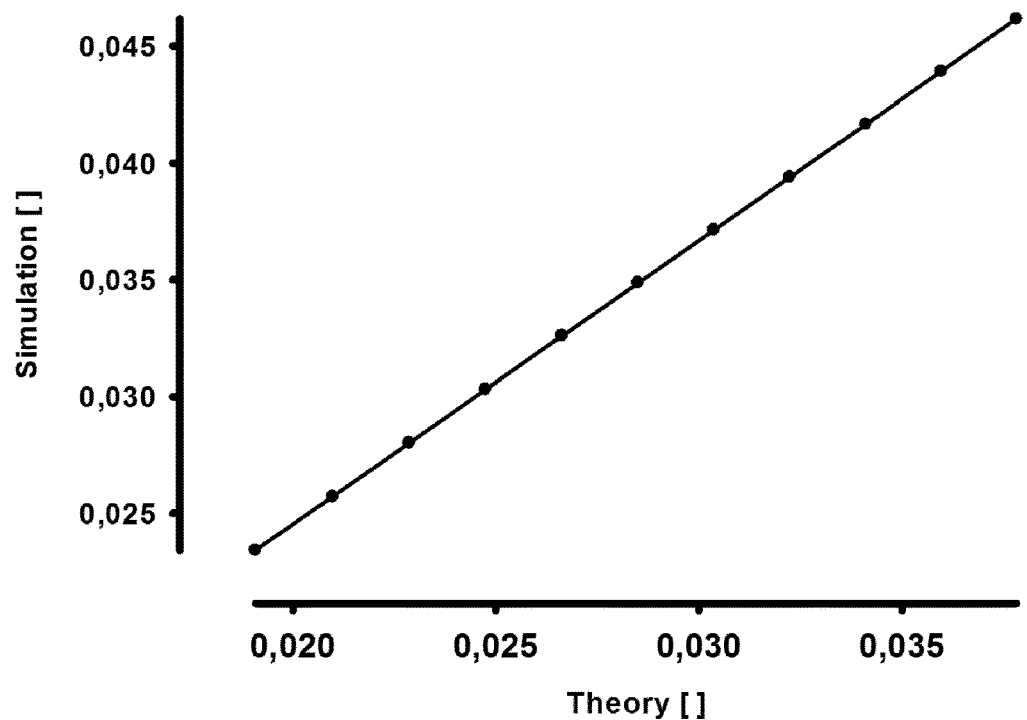
Figure 59:
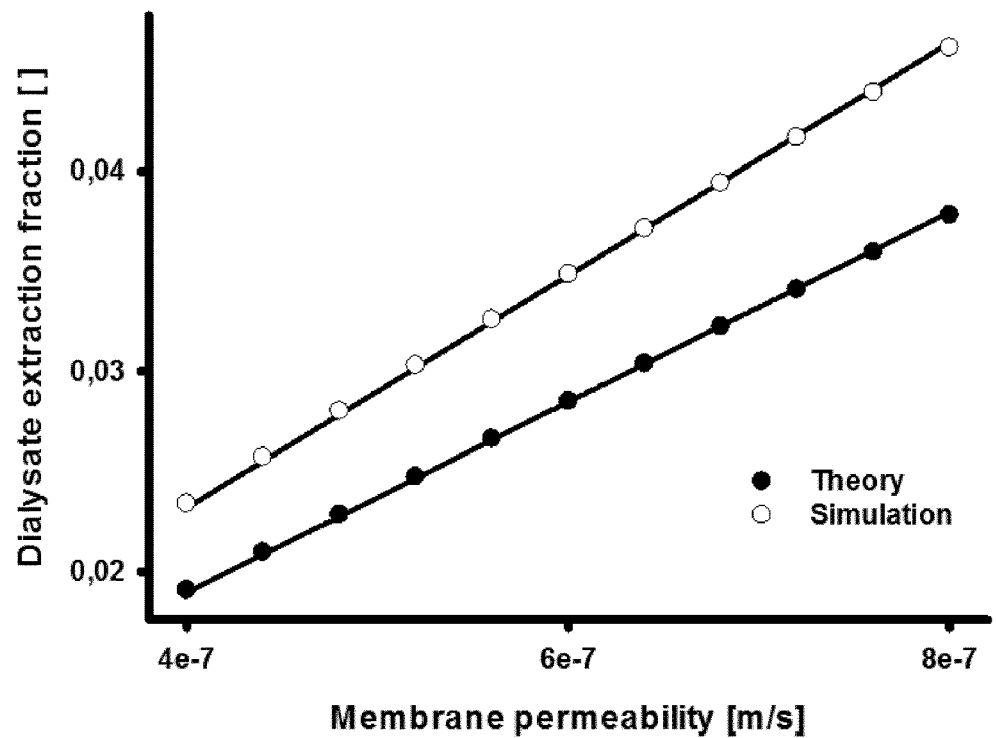
Figure 60:
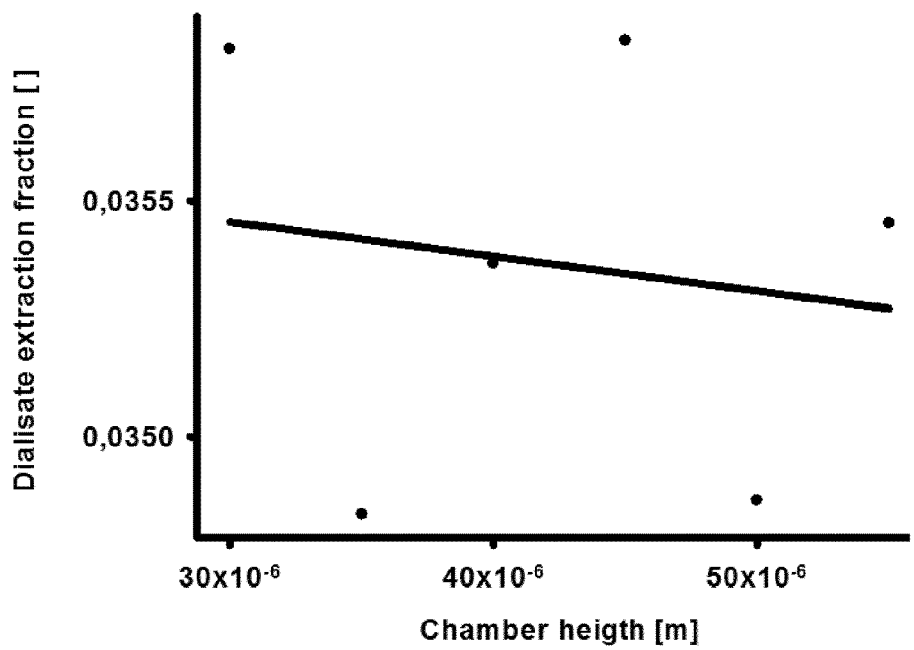
Figure 61:
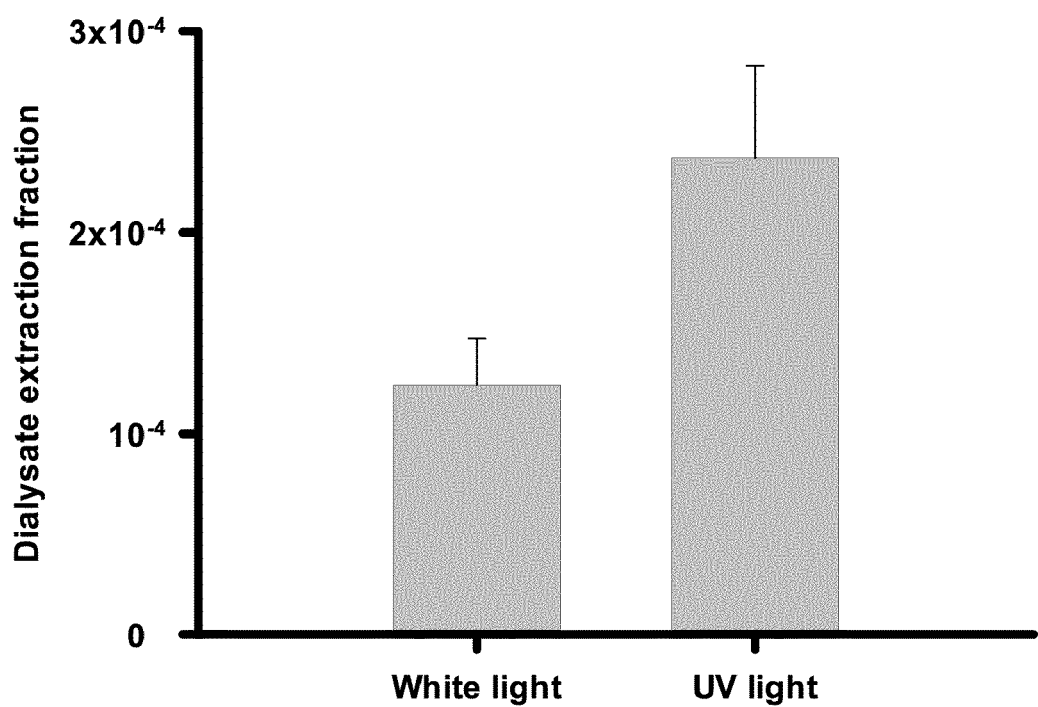

FIG. 29 same as in FIG. 28 simulated with a high permeability of the membrane;

FIG. 30 shows the total dialysate extraction fraction at the outlet of the diffusion chamber as determined from the theory or from a FEM simulation. The two results are linearly proportional $R^2$=9.99999;

FIG. 31 shows that in the application range the dialysate extraction fraction is linearly proportional to the membrane permeability $R^2$=9.99997;

FIG. 32 shows the glucose concentration measurement with a standard fluorimeter and the kinetic enzymatic UV-method. The upper bound and the lower bound, between which 95% of the measurements should be located, are also shown (±2*RMSE);

FIG. 33 shows the glucose concentration measurement with a microfluidics microfluorimeter. The upper bound and the lower bound between which 95% of the measurements should be located are also shown (±2*RMSE);

FIG. 34 shows the permeability change of a plasma-induced spirobenzopyran and PHEMA coated track-edged polycarbonate membrane (pore diameter: 200 nm);

FIG. 35 shows a glucose diffusion experiment through taped pig skin from the ear. The absorption of light is proportional to the glucose concentration;

FIG. 36 shows a schematical view (not to scale) of an embodiment of the device according to the invention;

FIG. 37 shows a schematical view (not to scale) of the probe head of FIG. 36 positioned on an infant;

FIG. 38 shows a perspective view of the probe head of FIGS. 36 and 37;

FIG. 39 shows an exploded view of the probe head of FIGS. 36 to 38;

FIG. 40 shows a view of a top side of the probe head of FIG. 39 which faces away from the membrane;

FIG. 41 shows a cross sectional view along the line A-A of FIG. 40;

FIG. 42 shows the detail C of FIG. 41;

FIG. 43 shows a view of the diffusion chamber of the probe head of FIG. 38 (without membrane);

FIG. 44 shows a plan view onto the diffusion chamber of the probe head;

FIG. 45 shows a cross sectional view along the line A-A of FIG. 44;

FIG. 46 shows the detail B of FIG. 45;

FIG. 47 shows an exploded view of an embodiment of the probe head according to the invention wherein an analyzing means in the form of a microfluidic chip is integrated into the probe head;

FIG. 48 shows a plan view onto the upper side of the probe head of FIG. 47;

FIG. 49 shows a plan view of the probe head of FIGS. 47 and 48;

FIG. 50 shows the diffusion chamber of the probe head of FIGS. 47 to 49;

FIG. 51 shows a modification of the device according to the invention of FIG. 16 with an extra vacuum pump with a vacuum regulator in the end, FIG. 52 shows an SEM micrograph of a mold for a microfluidic chip of the kind shown in FIGS. 17 and 47;

FIG. 53 shows an SEM micrograph of a mold for a microfluidic chip of the kind shown in FIGS. 17 and 47;

FIG. 54 shows an SEM micrograph of a mold for a diffusion (microdialysis) chamber of the kind shown in FIG. 47;

FIG. 55 shows the 3D flow streamlines inside the diffusion chamber of the probe head shown in FIGS. 36 to 46, the flow being laminar;

FIG. 56 shows a cross-section of a model of the diffusion chamber of the kind in FIG. 38, 44 showing the local dialysate extraction fraction having values between 0 (no substance extracted) and 1 (same concentration as in the blood). Shown are the results from a 3D Finite Element Method with a high permeability of the membrane;

FIG. 57 shows a cross-section of a model of the diffusion chamber of the kind in FIG. 38, 44 showing the local dialysate extraction fraction having values between 0 (no substance extracted) and 1 (same concentration as in the blood). Shown are the results from a 3D Finite Element Method with a lower permeability of the membrane;

FIG. 58 shows the total dialysate extraction fraction at the outlet of the diffusion chamber of the kind shown in FIGS. 38 and 44 as determined from the theory or from a FEM simulation. The two results are linearly proportional $R^2=1$;

FIG. 59 shows that in the application range the dialysate extraction fraction at the outlet of the diffusion chamber of the kind shown in FIGS. 38 and 44 is linearly proportional to the membrane permeability for both the theory $R^2=0.9996$ and the simulation $R^2=0.9998$;

FIG. 60 shows that as predicted from the theory, the dialysate extraction fraction at the outlet of the diffusion chamber of the kind shown in FIGS. 38 and 44 does not depend on the height if the diffusion chamber in the 3D FEM simulation. There is no significant correlation between the chamber height and the dialysate extraction fraction. The differences in the dialysate extraction fraction between the different points come from computing errors; and FIG. 61 shows the dialysate extraction fraction of a probe head of the kind of FIG. 36-46 measured with two different states, once exposed with white light, once exposed with UV light.

Figure 1:
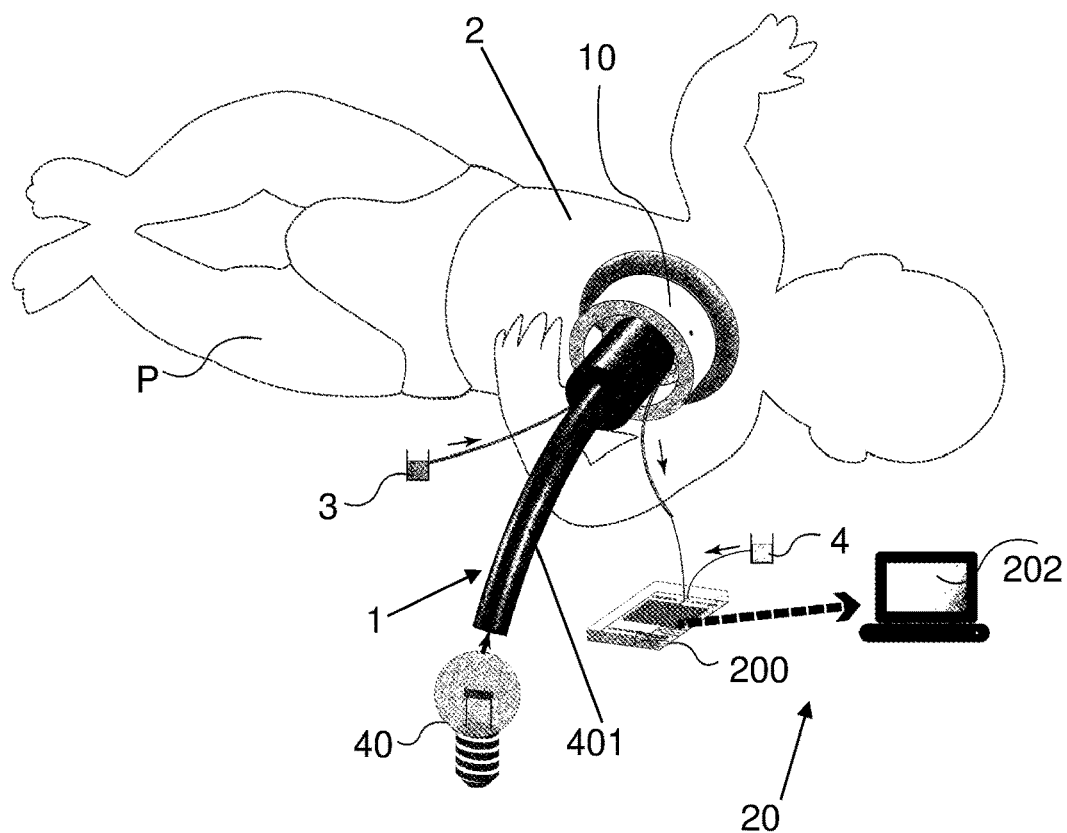

FIG. 1 shows a schematical illustration of a device 1 according to the invention. The device 1 comprises a probe head 10 (cf. also FIG. 4) comprising a diffusion chamber (also denoted as microdialysis chamber) 100 delimited by a membrane 30 for contacting the skin 2 of a patient P, wherein the diffusion chamber 100 comprises an inlet 101 as well as an outlet 102 for feeding a perfusion medium 3 into the diffusion chamber 100 and for discharging it out of the diffusion chamber 100, wherein the outlet 102 is connected to an analyzing means 20 for measuring the concentration of an analyte (e.g. glucose) in a perfusion medium 3, which analyte diffused through the membrane 30 in a first state of the latter, as well of the analyte in the perfusion medium 3, when the analyte diffused through the membrane 30 in a second state of the membrane, wherein the permeability of the membrane 30 with respect to said analyte differs in said two states such that the two concentrations of the analyte differ.

Further, reagents 4 are provided for the ex-vivo measurement of the concentration of the analyte in said mixture with the perfusion medium 3 that flows to the analyzing means 20. For measuring said concentrations, the analyzing means 20 preferably comprises a microfluorimeter (optional if a different concentration measurement is chosen) 200, which comprises a microfluidic chip 201 that determines the glucose concentration, as well as a computer 202 or a dedicated embedded computer for computing the glucose concentration from the microfluorimeter 200, for displaying it, and for controlling an excitation for switching the membrane 30 from the first state to the second state and vice versa. Preferably, the membrane 30 is switched to the first state by irradiating it by means of a light source 40 with light, particularly UV light, having a first wavelength, preferably in the range from 300 nm to 400 nm, and to the second state by irradiating it by means of the light source 2 with light, particularly visible light, having a second wavelength, particularly in the range from 500 nm to 650 nm.

Figure 2:
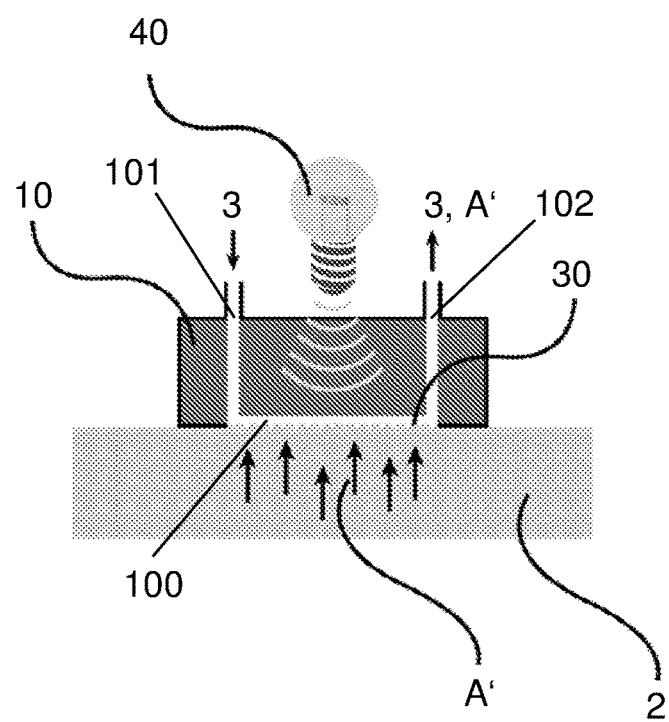
FIG. 2 shows a schematical cross section (not to scale) of a probe head of the device according to the invention.

FIG. 2 shows a schematical cross section of the probe head 10 of the device 1 according to the invention. According thereto, the light source 40 can be either embedded directly into the probe head 10 or can be located remotely and connected to the probe head 10 with a light guide 401. When the probe head 10 contacts the skin 2 of the patient P, said analytes (e.g. glucose) A' of the ex-vivo body fluid of the patient P can diffuse through the membrane 30, which delimits the diffusion chamber 100, into the chamber 100.

Figure 3:
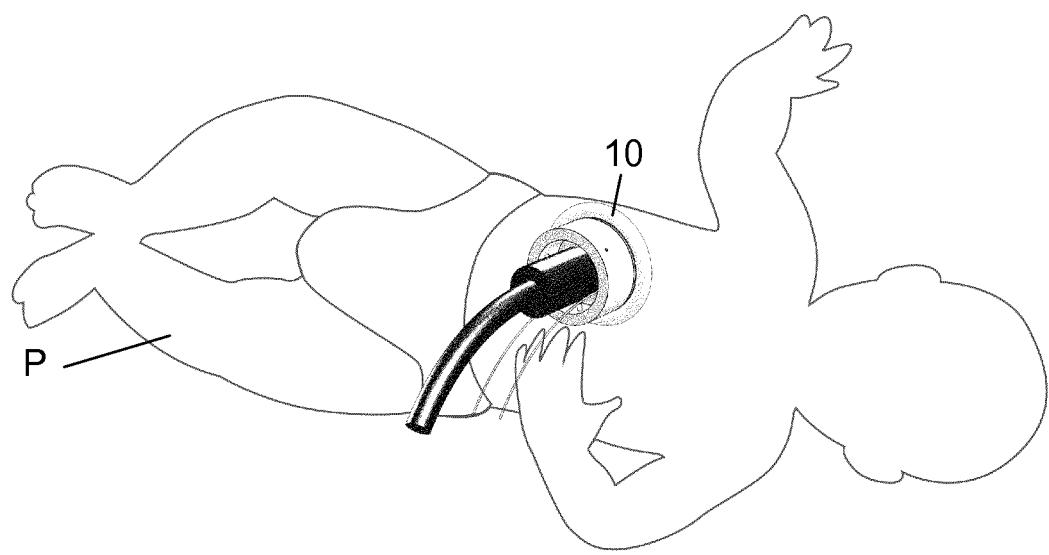
FIG. 3 shows a schematical view (not to scale) of the probe head positioned on an infant.

As can be seen from FIG. 3, preferably merely the probe head 10 comes into contact with the patient P.

FIGS. 4 to 15 show a preferred embodiment of the probe head 10 of the device 1 according to invention.

The probe head 10 comprises a body 11 (cf. FIG. 6) that is preferably formed out of a UV transparent PMMA. The body 11 comprises a first recess 12 on a rear side of the body 11 for insertion of a free end 401a of the light guide 401 designed to guide UV/visible light from the light source 40 to the membrane 30, which light guide 401 can be positioned and fastened with respect to the body 11 by means of three screws 402 protruding through associated apertures 403 (cf. FIG. 12) having matching threads into said first recess 12 so that the free end 401a can be clamped by means of said three screws 402. The body 11 further comprises a U-shaped second recess 100 forming said diffusion chamber 100 on a front side of the body facing away from said rear side (cf. FIGS. 8, 9, 13 and 14), which second recess 100 is covered by said light switchable membrane 30 which is releasably clamped to the body 11 by means of an elastic O-ring 13 that is arranged in a circumferential groove 14 formed an a lateral side of said body 11 when fastening the membrane 30 to the body 11 so as to cover the second recess/inflation chamber 100 with the membrane 30 (cf. FIGS. 6, 7, 9, and 10). The switchable membrane 30 could also be releasably self-glueing itself to the probe head 10, therefore not requiring the elastic O-ring 13 and the circumferential groove 14.

Figure 4:
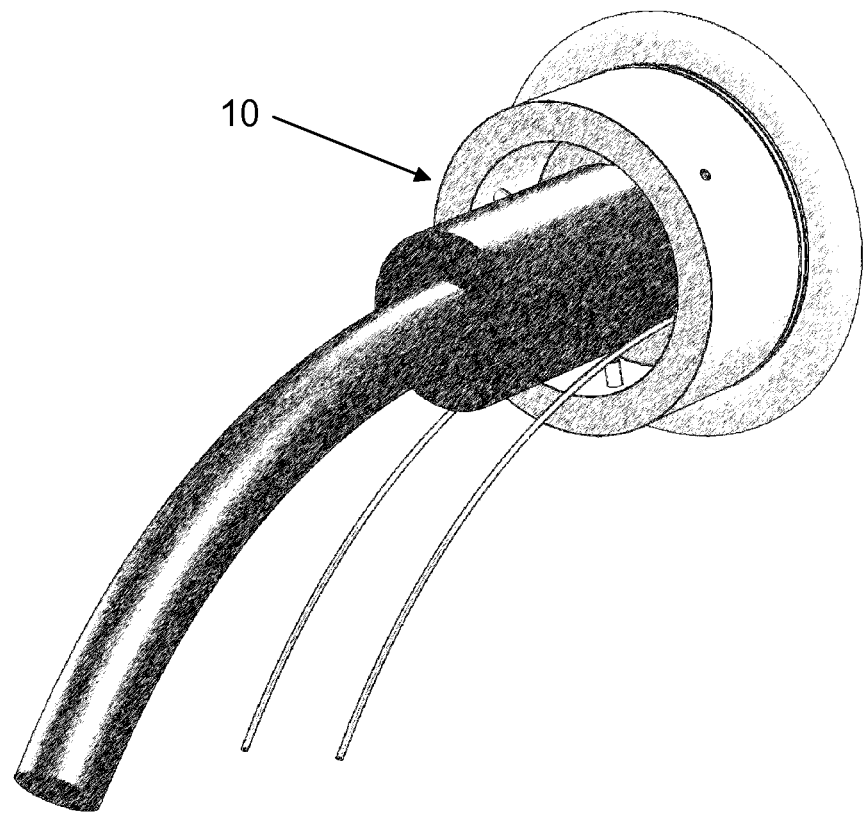
FIG. 4 shows a perspective view of a probe head of a device according to the invention.
Figure 5:
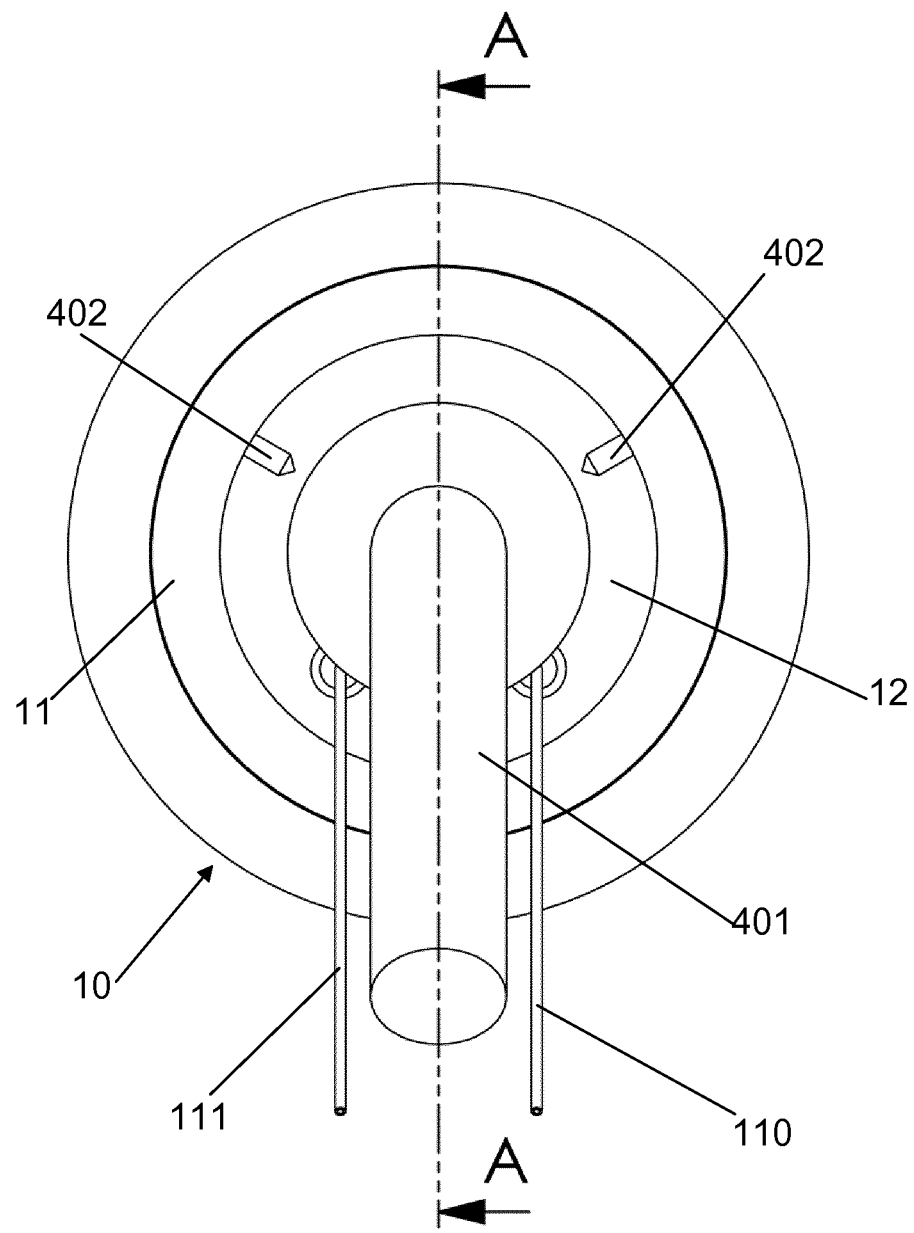
FIG. 5 shows a top view of the probe head shown in FIG. 4.
Figure 6:
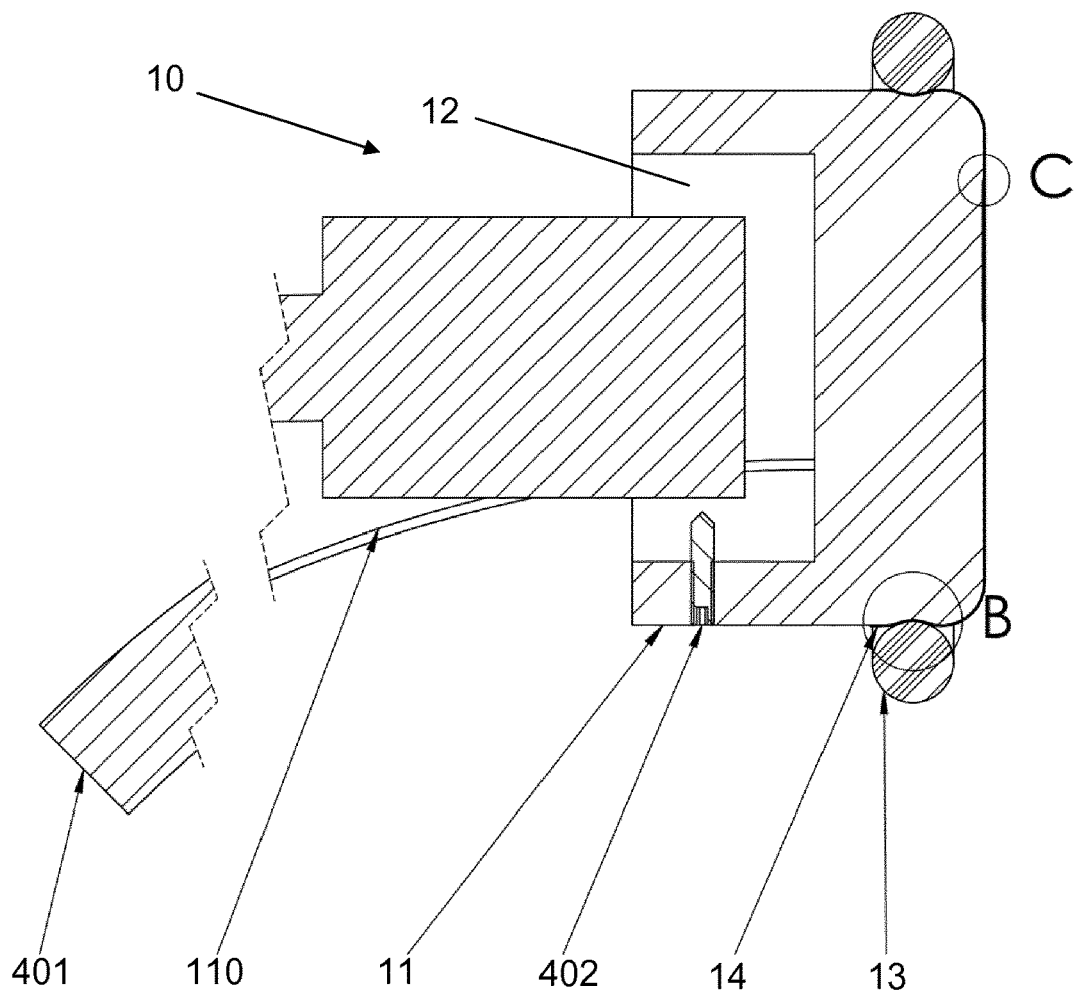
FIG. 6 shows a cross sectional view of the probe head along the line A-A of FIG. 5.
Figure 7:
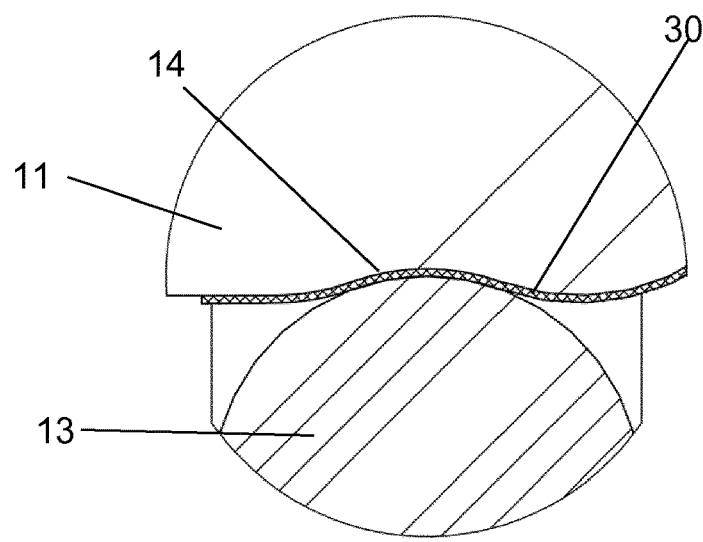
FIG. 7 shows a cross sectional view of the probe head detail encompassed by circle B of FIG. 6.
Figure 8:
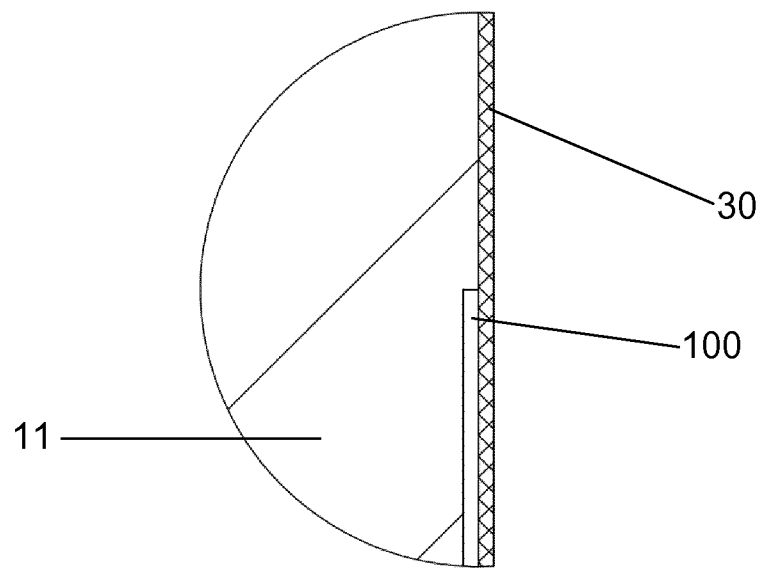
FIG. 8 shows a cross sectional view of the further probe head detail encompassed by circle C of FIG. 6.
Figure 9:
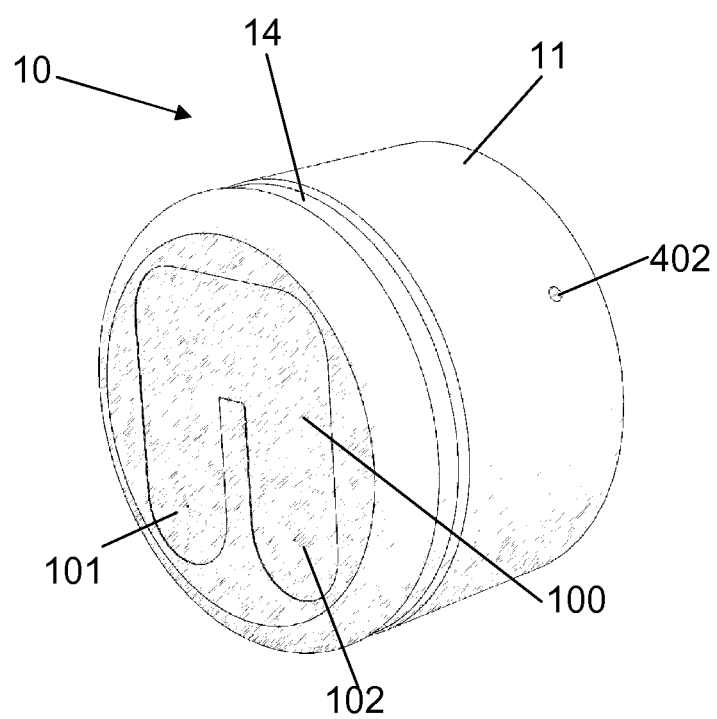
FIG. 9 shows a perspective view of a part of the probe head containing the diffusion chamber.
Figure 10:
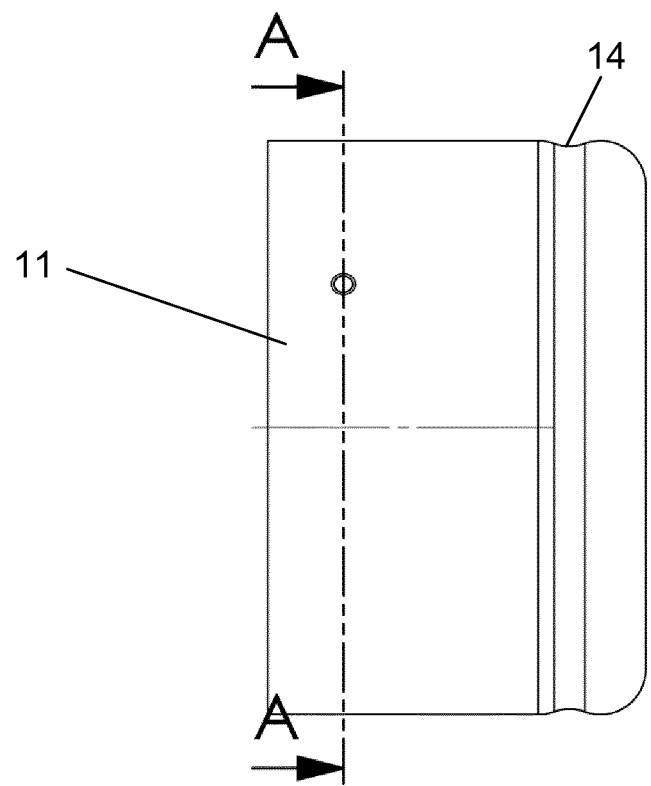
FIG. 10 shows a lateral view of the part shown in FIG. 9.
Figure 11:
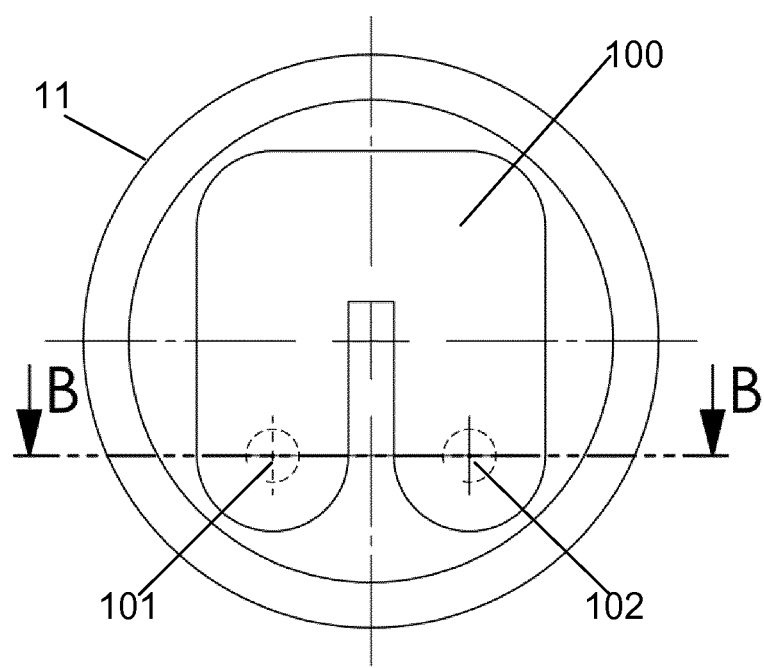
FIG. 11 shows a plan view onto the diffusion chamber according to FIG. 9.
Figure 12:
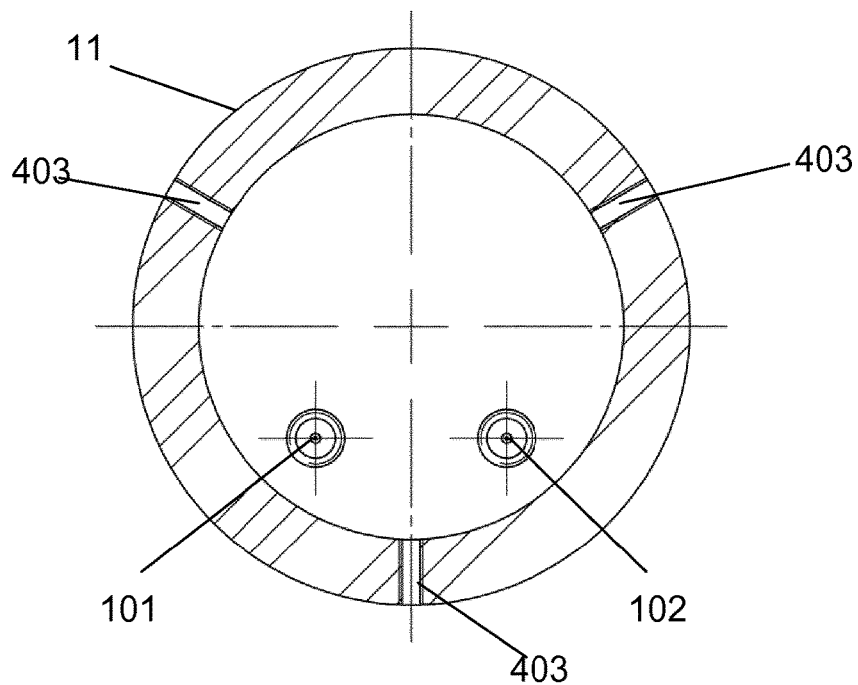
FIG. 12 shows a cross section A-A of FIG. 10.
Figure 13:
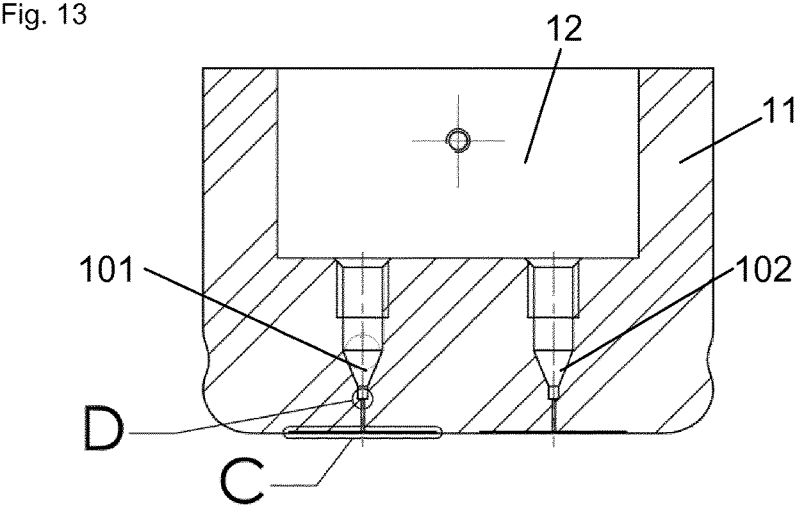
FIG. 13 shows a cross section B-B of FIG. 11.
Figure 14:
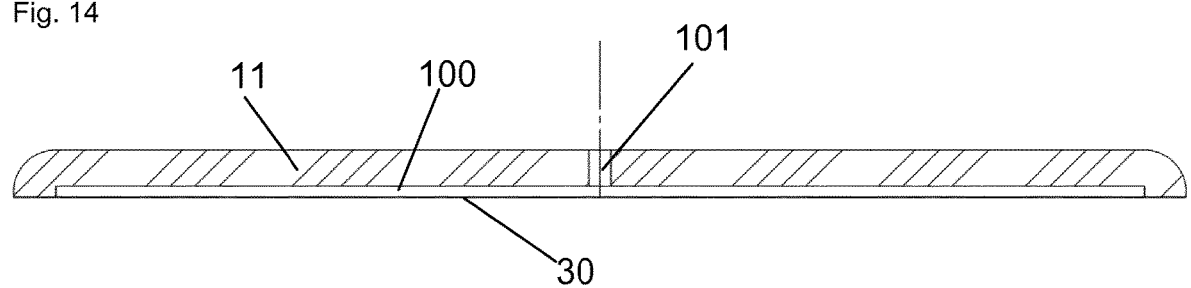
FIG. 14 shows detail C of FIG. 13.
Figure 15:
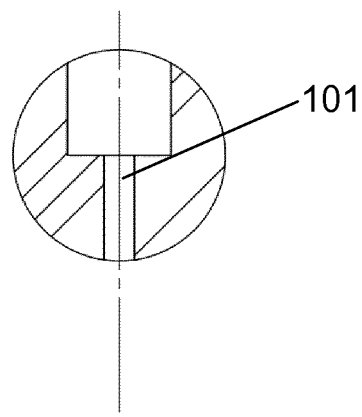
FIG. 15 shows detail D of FIG. 13.

As shown in FIGS. 4, 5, and 6 the probe head 10 further comprises a first conduit 110 being in flow connection to said inlet 101 as well as a second conduit 111 being in flow connection with to said outlet 102, wherein said inlet 101 and outlet 102 are formed in a bottom of said first recess, wherein said inlet 101 and said outlet 102 are formed as through-openings each opening out into an end of said U-shaped diffusion chamber 100 as shown in FIGS. 12, 13, 14 and 15.

For determining the actual concentration of the analyte in the blood of the patient P, the ex-vivo analytes passively diffusing through the skin and the membrane 30 are analyzed. For this, these analytes are carried away from the probe head 10 to the analyzing means 20 by means of the perfusion medium 3. Appropriate analysis allows the measurement of analyte concentration in the perfusion medium 3. Thereafter, light as external stimulus is applied to change the diffusion resistance of the membrane, i.e., the membrane 30 is brought from the first state into its second state. After a second run of analyte analysis the blood analyte level can be calculated from the two consecutive concentration measurements with the different membrane states.

For glucose analysis, the glucose containing perfusion medium/fluid can be mixed with an enzymatic solution for the stoichiometric conversion of glucose by the analyzing means 20. This final solution will then be spectroscopically analysed by a fluorimeter of the analyzing means 20. This is transferred into the microfluidic chip 201 connected to the outlet 102 of the probe head 10 as shown in FIGS. 1 and 16.

FIG. 16 shows a block diagram of a device 1 according to the invention. The perfusion medium 3 is pumped via a particle filter 114 and a liquid flow meter 115 through inlet 101 into the diffusion chamber 100 of the probe head 10 and transports the analyte to the analyzing means 20, namely to the microfluidic chip 201 of the microfluorimeter 200 that is designed to measure the clucose concentration in the repective perfusion medium 3. Since a known flow of perfusion medium 3 is used, the concentration of the analyte in the respective fluid 3 can be determined by the analyzing means 20.

Further, the reagents or reagent fluid 4 (preferably a Hexokinase/Glucose-6-phosphate deydrogenase/ATP/buffer/Mg2+ solution in water) for the ex-vivo measurement of the concentration that flows to the microfluorimeter 200 (both optional if a different concentration measurement is chosen; the analyzing means should just allow to monitor preferably continuously (or almost) the concentration within the required range with sufficient precision) are pumped via a flow meter 116 and a particle filter 117 to the microfluorimeter 200 of the analyzing means 20.

The microfluidic chip 201 that determines the respective glucose concentration is connected to a computer or a dedicated embedded computer for computing the glucose concentration from the two concentrations for the two different membrane states as measured by the microfluorimeter 200. The computer 202 is further designed to display the computed concentration of the analyte in the blood of the patient P, as well as for controlling the switching means (light source 40) that switches the membrane 30 between the two states. Analyzed dialysate is discharged into a waste container 203.

Further, the air compressor 120 or compressed air line, the precision air pressure regulators 118 (e.g. with feedback and vent), as well as the air pressure measurement devices 119 allow a pressure driven flow of the perfusion medium 3 through the probe head 10/diffusion chamber 100 into the microfluorimeter 200 and of the reagent fluid 4 into said microfluorimeter 200 with a very low pressure variation, leading to a very low flow variation and thus a very small error in equation (9) below. The pressure from the air compressor/compressed air line 120 is brought to two the two precision pressure regulators 118 so that the two reservoirs 3, 4 for the reagent fluid and the perfusion medium (or perfusate) are pressurized. Controlling now the pressure difference of each reservoir 3, 4 in comparison with the pressure of the analyzing means outlet (at the atmospheric pressure) the pressure difference will drive laminar flows into the probe head 10, tubing, and the microfluidic chip.

As already introduced above, Fick's law models the passive diffusion across the skin of the patient and the membrane 30:

$$C_{g,body} - C_{g,sensor} = F_g(R_g + R_m) \quad (1),$$

where $C_{g,body}$ is he blood glucose concentration, $C_{g,sensors}$ the glucose concentration in the diffusion chamber 100, $F_g$ the glucose flow through the skin and the membrane 30, $R_g$ the skin resistance to glucose diffusion, $R_m$ the membrane resistance to glucose diffusion which has two values, one for each state. The unknowns are the blood glucose concentration $C_g$ and the skin resistance to glucose diffusion $R_g$. With measuring the concentration and the glucose diffusion flow for two membrane resistances, both the skin resistance and the blood glucose concentration can be determined.

So to keep the concentration gradient high, and thus the glucose diffusion flow high, the sensor is flushed with said perfusion medium in the above described microdialyis setup. Thus, once integrated over the flow streamline through the diffusion chamber 100 equation (1) becomes:

$$C_{g,sensor} = \left(1 - \exp\left[-\frac{A_m}{Q_d(R_g + R_m)}\right]\right) C_{g,body} \quad (2)$$

the term $$\left(1 - \exp\left[-\frac{A_m}{Q_d(R_g + R_m)}\right]\right) \quad (3)$$

is also called the dialysate extraction fraction, where Qd ist he dialysate flow and Am the microdialysis chamber area in contact with the membrane.

If $$Q_d \frac{R_g + R_m}{A_m} \gg \frac{1}{2}$$

the dialysate extraction fraction in (3) can be linearized. Then Eqn. (2) becomes:

$$C_{g,sensor} = \frac{A_m}{Q_d} \frac{1}{R_g + R_m} C_{g,body} \tag{4}$$

Then, with measuring the two analyte concentrations $C_{ml}$ and $C_{mh}$ for two corresponding membrane states, or two membrane resistance values $R_{ml}$ and $R_{mh}$, one gets the blood glucose concentration, from (4):

$$C_{g,body} = \frac{Q_d}{A_m}(R_{mh} + R_{ml}) \frac{C_{ml} C_{mh}}{C_{ml} - C_{mh}} \tag{5}$$

The theoretical measurement errors are calculated as follows:

$$\Delta C_{G,Body} = \frac{Q_d}{A_m} \sqrt{\left(\frac{(R_g + R_{ml})^2}{R_{mh} - R_{ml}}\right)^2 + \left(\frac{(R_g + R_{mh})^2}{R_{mh} - R_{ml}}\right)^2} \Delta C_{g,sensor} \tag{6}$$

$$\frac{\Delta C_{g,body}}{C_{G,body}} = +\frac{1}{R_{mh} - R_{ml}} \Delta R_{ml} \tag{7}$$

$$\frac{\Delta C_{g,body}}{C_{G,body}} = -\frac{1}{R_{mh} - R_{ml}} \Delta R_{mh} \tag{8}$$

$$\frac{\Delta C_{G,Body}}{C_{G,Body}} = \frac{\Delta Q_d}{Q_d} \sqrt{\left(\frac{R_g + R_{ml}}{R_{mh} - R_{ml}}\right)^2 + \left(\frac{R_g + R_{mh}}{R_{mh} - R_{ml}}\right)^2} \tag{9}$$

$$\frac{\Delta C_{G,Body}}{C_{G,Body}} = \frac{\Delta C_{G,sensors}}{C_{G,sensors}} \sqrt{\left(\frac{R_g + R_{ml}}{R_{mh} - R_{ml}}\right)^2 + \left(\frac{R_g + R_{mh}}{R_{mh} - R_{ml}}\right)^2} \tag{10}$$

Thus, with the following values ($R_g$ is approximate), a negligible $R_{ml} \ll R_{mh}$, $R_{mh} = R_g$:
$R_G = 1,200,000$ scm$^{-1}$
$Q_d = 5$ µL min$^{-1}$
$A_m = 4$ cm$^2$ The equations 6-10 give:

$$\Delta C_{GB} = 200 \Delta C_{meas}$$

$$\frac{\sigma_{meas}}{C_{meas}} < 0.32\%$$

$$\frac{\sigma_{Q_d}}{Q_d} < 0.32\%$$

$$\frac{\sigma_{R_{mh}}}{R_{mh}} < 0.32\%$$

$$\frac{\Delta C_{g,body}}{C_{G,body}} = \frac{\Delta R_{mh}}{R_{mh}}$$

The principle of the microfluidic chip 201 for concentration measurement by means of with fluorescence measurement is shown in FIG. 17. The chip 201 is preferably made out of polydimethylsiloxane (PDMS) that is molded onto a SU-8 on silicon mold fabricated by a non-standard photo-lithographic process described in detail in [1]. The chip 201 may also be made out of polycarbonate (PC), e.g., by means of injection molding. The chip 201 uses continuous flow rates. It first passively mixes the diluted analytes in the dialysate (e.g. in the respective mix with the perfusion medium 3) with reagent fluid 4 for the standard hexokinase glucose assay. The mixing duration with passive diffusion is negligible compared with the reaction lag time. Thus, the enzymatic reaction is not diffusion limited and follows a pseudo-first-order reaction kinetic. There is a delay channel (60 s) 24 for the lag time of the coupled enzyme reaction. The fabricated channel height is controlled and uniform so that the delays in the channels are not altered. With a channel uniformity of ±2.5% on thick structures this is a non-standard fabrication process with multilayers UV patterned SU-8 photoresist using only the central part of the silicon wafer for the mold. The flow inside the channels is kept laminar so that little transverse mixing occurs, i.e., so that the flow is uniform over the channel length.

In detail, as shown in FIG. 17, the microfluidic chip 201 for monitoring the glucose concentration in the dialysate comprises a reagent inlet 21 for the reagent fluid 4, a dialysate inlet 22 used for said dialysates, a micromixer 23 for mixing dialysate and reagent fluid 4, said delay channel 24, a the first fluorescence chamber 25, a second delay channel 26, a second fluorescence chamber 27, as well as a waste outlet 28 for discharging the measured dialysate.

Figure 18:
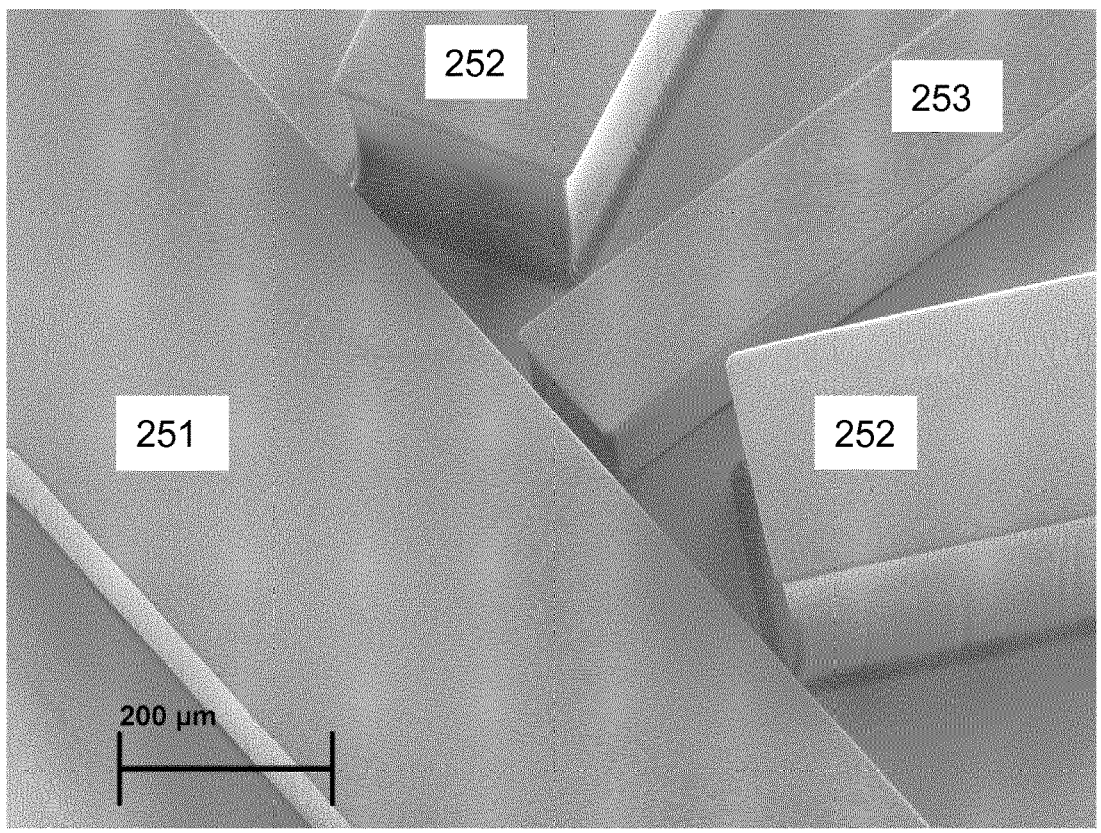
FIG. 18 shows a mold for a microfluidic chip of the kind shown in FIG. 17.

FIG. 18 shows the fluorescence chamber 25 of the manufactured mold with the probed volume 251, the visible light (VIS) fluorescence emission collection fibers 252 and the ultra-violet UV fluorescence excitation light 253.

Figure 19:
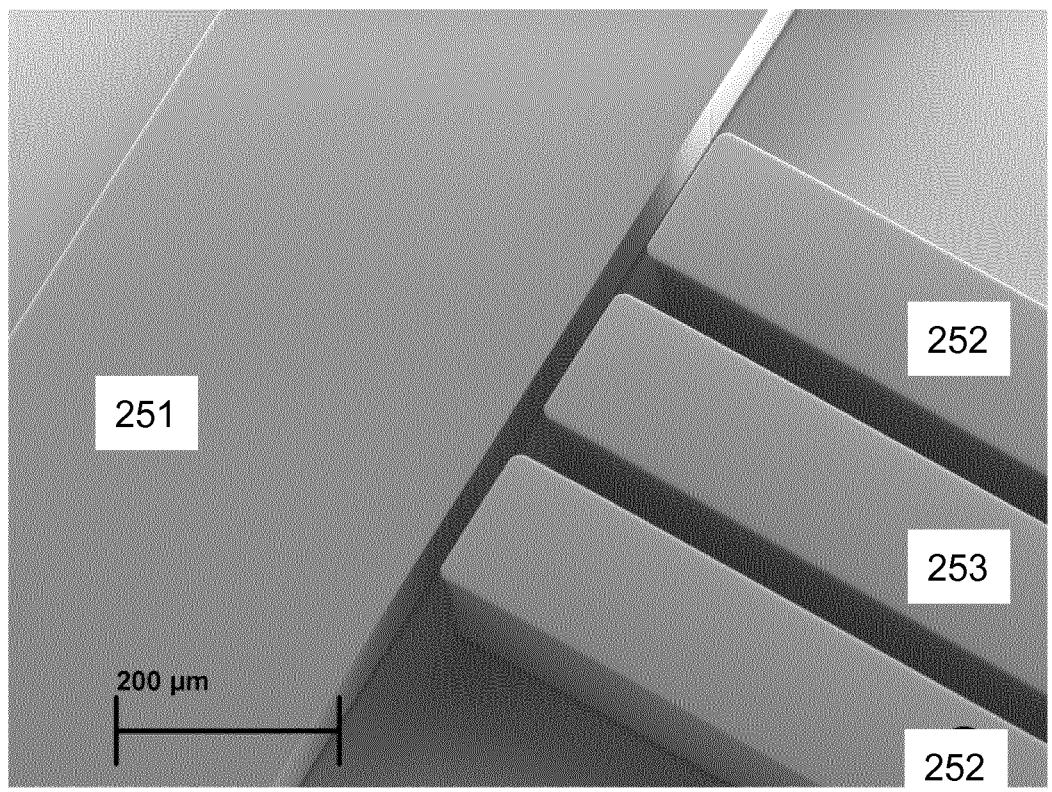
FIG. 19 shows a mold for a microfluidic chip of the kind shown in FIG. 17.

FIG. 19 shows a variation of the fluorescence chamber 25 of the manufactured mold with probed volume 251, the visible light (VIS) fluorescence emission collection fibers 252 and the ultra-violet UV fluorescence excitation light 253.

After the first delay channel 24, the pseudo-first order reaction is monitored by the fixed-point method using the two fluorescence chambers 25, 27 separated by the 7 s second delay channel 26. The difference between the two fluorescence signals of the enzymatic reaction product is proportional to the glucose concentration. The fluorescence chamber 25 has three embedded optical fibers, one for the fluorescence excitation of at 340 nm, and two for the emission at 450 nm. The excitation comes from a filtered UV lamp, a laser, or a LED and the emission is measured on a cooled silicon photomultiplier (SiPM).

In this specific example, two different wavelengths were used to change from the first state of permeability of the membrane 30 to the second one.

As photochromic compounds spirobenzopyran- and spirooxazine-compounds were used as shown in FIGS. 20 to 26.

The spirocompounds were integrated in the grafted polymer either by copolymerization of an acrylate derivative of the spirocompound with MMA (methyl methacrylate), AEMA (aminoethyl methacrylate), HEMA (hydroxyethyl methacrylate) or HEA (hydroxyethyl acrylate), HEA-TMS ([trimethylsilyloxy]hydroxyethyl) or PDMS ((α,ω)-methacryloxypropyl poly(dimethylsiloxane)) or by postmodification of a grafted PAEMA (poly(N-amino)ethyl methacrylate), PHEMA (polyhydroxyethyl methacrylate) or PHEA (polyhydroxyethyl acrylate) layer or polymer network with a carboxylic acid derivative of the spirocompound.

Figure 20:
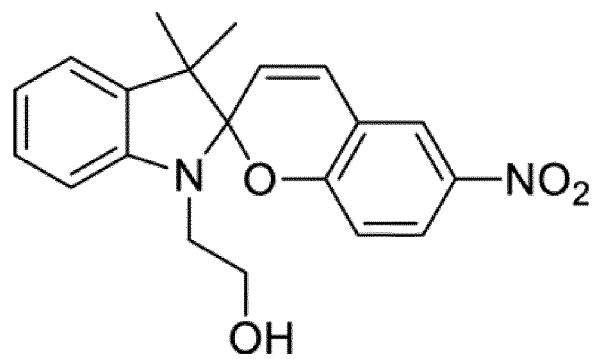
FIG. 20 shows a synthesized spiro-compound SP5 (2-(3',3'-dimethyl-6-nitro-spiro[chromene-2,2'-indoline]-1'-yl) ethanol) that can be used in the present invention.

FIG. 20 shows a synthesized spiro-compound SP5 according to a first example.

Figure 21:
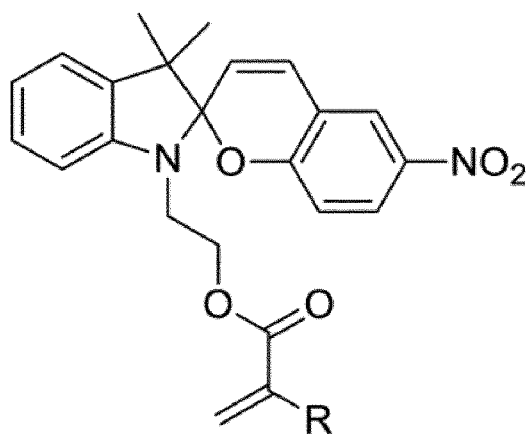
FIG. 21 shows a synthesized spiro-compound SP7 with R=Me (2-(3',3'-dimethyl-6-nitro-spiro[chromene-2,2'-indoline]-1'-yl)ethyl 2-methylprop-2-enoate) and SP9 with R=H (2-(3',3'-dimethyl-6-nitro-spiro[chromene-2,2'-indoline]-1'-yl)ethyl prop-2-enoate) that can be used in the present invention.

FIG. 21 shows a synthesized spiro-compound SP7 with R=Me and SP9 with R=H according to a second and third example.

Figure 22:
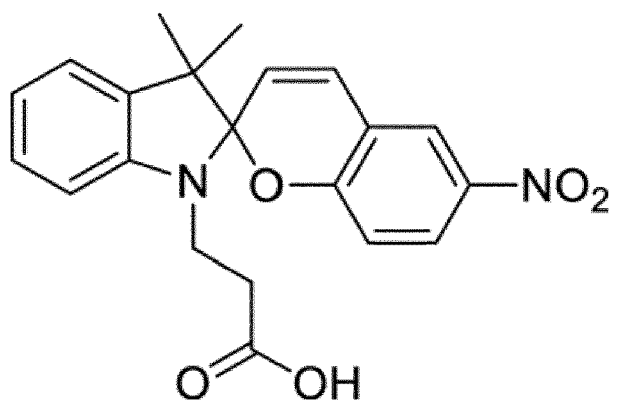
FIG. 22 shows a synthesized spiro-compound SP12 (3-(3',3'-dimethyl-6-nitro-spiro[chromene-2,2'-indoline]-1'-yl) propanoic acid) that can be used in the present invention.

FIG. 22 shows a synthesized spiro-compound SP12 according to a fourth example.

Figure 23:
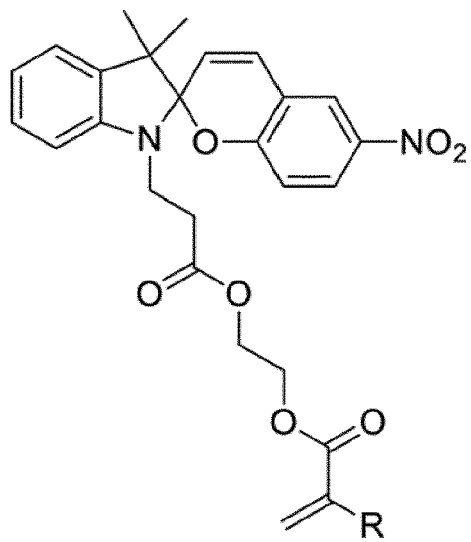
FIG. 23 shows a synthesized spiro-compound SP14 with R=Me (2-[3-(3',3'-dimethyl-6-nitro-spiro[chromene-2,2'-indoline]-1'-yl)propanoyloxy]ethyl 2-methylprop-2-enoate) and SP16 with R=H (2-prop-2-enoyloxyethyl 3-(3',3'-dimethyl-6-nitro-spiro[chromene-2,2'-indoline]-1'-yl)propanoate) that can be used in the present invention.

FIG. 23 shows a synthesized spiro-compound SP14 with R=Me and SP16 with R=H according to a fifth and sixth example.

FIG. 23 shows a synthesized spiro-compound SO37 according to a seventh example.

Figure 24:
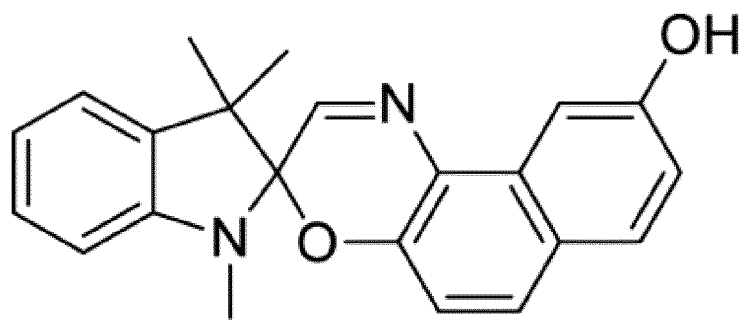
FIG. 24 shows a synthesized spiro-compound SO37 (1,3',3'-trimethylspiro[benzo[f][1,4]benzoxazine-3,2'-indoline]-9-ol) that can be used in the present used in the present invention.

FIG. 24 shows a synthesized spiro-compound SO39 with R=Me and SO50 with R=H according to an eighth and ninth example.

Figure 25:
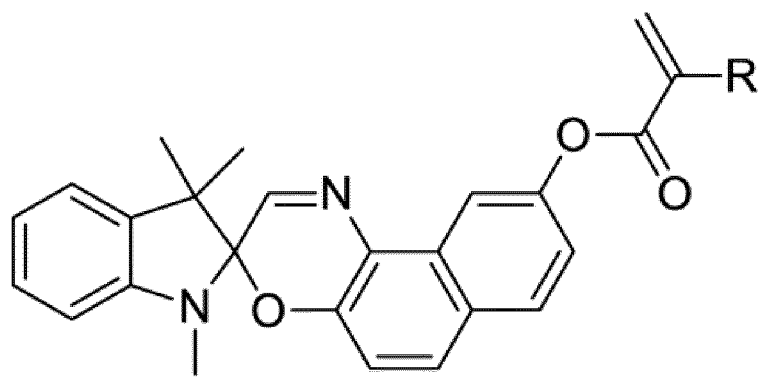
FIG. 25 shows a synthesized spiro-compound SO39 with R=Me ((1',3',3'-trimethylspiro[benzo[f][1,4]benzoxazine-3,2'-indoline]-9-yl) 2-methylprop-2-enoate) and SO50 ((1',3',3'-trimethylspiro[benzo[f][1,4]benzoxazine-3,2'-indoline]-9-yl) prop-2-enoate) with R=H that can be used in the present invention.
Figure 26:
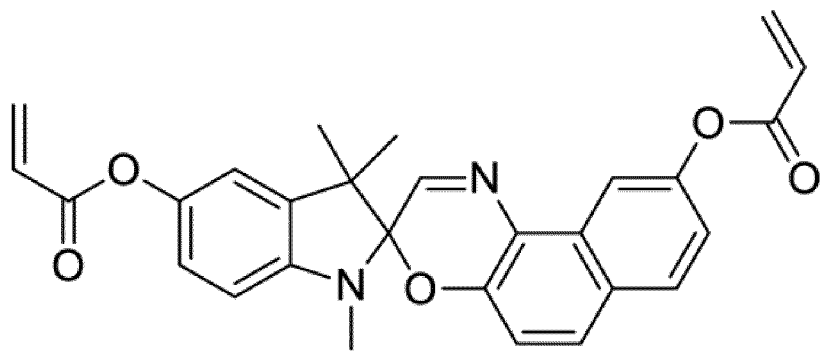
FIG. 26 shows a synthesized spiro-compound SO49 ((5'-acetoxy-1,3',3'-trimethyl-spiro[benzo[f][1,4]benzoxazine-3,2'-indoline]-9-yl) prop-2-enoate) that can be used in the present invention.

Finally, FIG. 25 shows a synthesized spiro-compound SO49 according to a tenth example.

The light-responsive membranes 30 were prepared in different ways:

Commercially available track-etched polycarbonate membranes with a pore size of 15 nm, 30 nm, 50 nm, 100 nm, 200 nm, 400 nm, 1000 nm were dip-coated with a polymer solution containing a co-polymer of a spirobenzopyran acrylate and PMMA. The spirobenzopyran acrylate monomer itself can also be polymerized. The co-monomer primarily serves for enhancing the effect of the spirobenzopyran switch and the photostability of the spiropyrans. The copolymer contained between 1-10% of spirobenzopyran according to FIG. 21 (the CAS-No. is 89908-23-6 for R=H and 25952-50-5 for R=CH$_3$) or FIG. 23. Best switching was observed with 4% of spirobenzopyran. Other membranes, which were coated, are track-etched polyester membranes and PVDF membranes which showed a lower permeability change. The permeability change was demonstrated with aqueous solutions of caffeine and glucose.

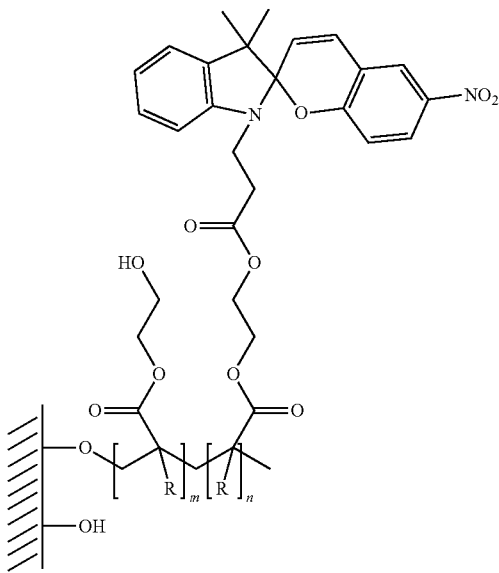

Further, plasma-induced graft surface polymerization of track-etched polycarbonate membranes with a pore size of 15 nm, 30 nm, 50 nm, 100 nm, 200 nm, 400 nm, 1000 nm were produced. A copolymer consisting of a spirobenzopyran acrylate and a comonomer (2-hydroxy acrylate, 2-hydroxy methacrylate, 2-amino methacrylate, methyl methacrylate) was grafted from a plasma treated membrane. The amount of spirobenzopyran in the grafted polymer was between 1-100%. Spirobenzopyran acrylate was replaced by spirooxazine acrylate in some experiments. The permeability change was demonstrated with aqueous solutions of caffeine and glucose.

Further, surface-induced atom transfer radical polymerization (SI-ATRP) was performed from track-edged polyester membranes with a pore size of 200 nm. A copolymer consisting of a spirobenzopyran acrylate and a comonomer (2-hydroxy acrylate (HEA), 2-hydroxy methacrylate (HEMA), 2-amino methacrylate (AEMA), methyl methacrylate (MMA)) was grafted from a plasma treated membrane. The amount of spirobenzopyran in the grafted polymer was between 0.4-13%. The permeability change was demonstrated with aqueous solutions of caffeine.

Further, amphiphilic co-networks were used as membranes consisting of poly (2-hydroxy ethylacrylate) as the hydrophilic domain and (α,ω)-methacryloxypropyl poly(dimethylsiloxane) (PDMS) as hydrophobic domain [2, recipe of amphiphilic conetwork without photochromic unit]. Membranes with different weight ratios (wt.-%) of HEA: PDMS (70:30, 60:40, 50:50, 40:60) and spirobenzopyran acrylate were produced (0.05-2 wt.-%). Spirobenzopyran was replaced by spirooxazine acrylate in some experiments. The permeability change was demonstrated with aqueous solutions of caffeine. In case the membrane 30 sticks only to the probe head 10, but not to the skin of the patient (e.g. in case of the amphiphilic co-network) the O-ring 13 may be omitted. Generally, the inlet and outlet 101, 102 (cf. FIG. 2 for instance) may also switch positions, with the outlet still being connected to the analyzing means 20.

The dimensions of the probe head 10 can of course be varied. The material can be changed, especially in case the switching stimulus of the membrane permeability is changed to e.g. electrical stimulation. Thus, transparency to UV-light would not be needed anymore.

A standard fluorimeter could be used instead of the microfluorimeter on a chip 201. It would also be connected with capillaries to the probe head 10. The material of the microfluidic chip 201 could also be changed. Instead of fluorescence, absorption spectroscopy could be used. Instead of SiPM, photomultiplier tubes or other sensitive photodetectors could be used. In general, any online glucose concentration accurate enough could be used instead of the enzymatic reaction. It also has to be changed if other metabolites have to be measured.

By including a drug into the perfusion medium 3, the device 1 could be used for controlled drug delivery.

The working principle of the sensor could also work by using side by side two membranes with different permeabilities instead of using an intelligent membrane which changes permeability by applying a stimulus. Such a change in permeability can be triggered either by a change of light, temperature, pH or electricity.

Other photochromic molecules, which could be integrated in a light-responsive membrane are:

Azobenzene

Coumarin, and

Dithienylethene.

Figure 27:
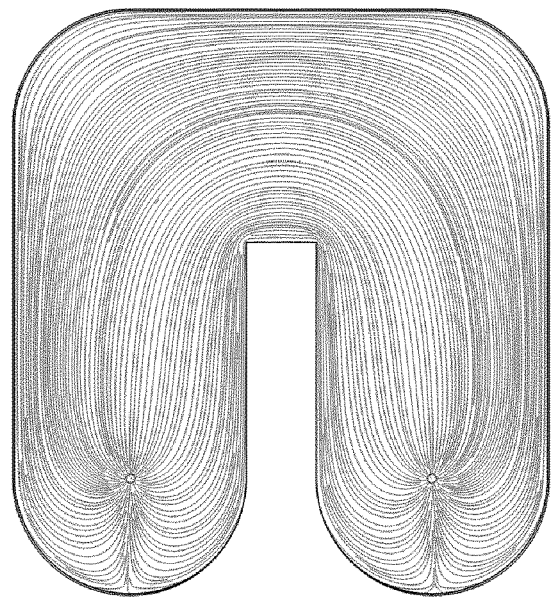
FIG. 27 shows the 3D flow streamlines inside the diffusion chamber as seen from the top, the flow being laminar.

Further, extensive Finite Element Method Simulations of the probe head 10 were conducted. The real 3D geometry was used for the simulation. The boundary conditions for the flow were chosen as follows: no-slip flow onto the chamber walls with pressure driven flow and a laminar flow pattern into the inlet 101 and atmospheric pressure at the outlet 102. The 3D pattern of the flow inside the microdialysis chamber 100 is laminar as shown in FIG. 27.

Further, FIG. 28 shows a cross-section of the diffusion chamber 100 showing the local dialysate extraction fraction with a dimensionless value between 0 (no substance extracted to 1 (same concentration as in the blood) as resulting from a 3D Finite Element Method with a low permeability of the membrane 30.

Further, FIG. 29 shows the same simulation as FIG. 28, but with a higher permeability of the membrane 30.

Diffusion of a glucose concentration of 5 mmol/L through the skin and the smart membrane 30 according to the invention was simulated with different permeability states. FIG. 30 shows a cross-section of the dialysate extraction fraction (concentration of the substance in the dialysate divided by the concentration of the same substance in the blood) pattern inside the diffusion chamber 100 with glucose diffused through a membrane 30 with a low permeability state. FIG. 31 shows the same with a high permeability state. FIG. 30 plots the dialysate extraction fraction at the outlet as simulated compared with the theory. The two are highly correlated $R^2$=0.99999, but the relation is not exactly one to one. The curved laminar flow pattern with decreased flow velocity closer to the walls explains the difference. This difference is good, because it means higher concentration to be measured continuously after the microdialysis head 10 and better accuracy.

FIG. 31 shows that the dialysate extraction fraction is highly linearly proportional $R^2$=0.99997 to the membrane permeability in the application expected range for glucose. This means we can use only two membrane states for measuring the blood glucose.

It has been shown that glucose concentration could be determined with the appropriate accuracy with a fluorimeter. FIG. 32 shows the fluorescence measurement with enzymatic reaction of very low glucose concentration.

Glucose concentration could be measured with the same principle using the microfluorimeter as shown in FIG. 33.

It was also demonstrated that the membrane permeability to glucose can be switched by exposure to UV light at 366 nm, as opposed to daylight. The results are shown in FIG. 34 using a plasma-induced spirobenzopyran and PHEMA coated track-edged polycarbonate membrane (pore diameter: 200 nm).

Finally, in-vitro testing with taped pigskin from the ear exhibited passive diffusion processes of glucose with a Franz cell experiment as shown in FIG. 35.

In the above, the glucose measurement was described as one possible application of the device 1 according to the invention, because it has a tremendous clinical value. However, the same principle can be applied to any analyte that diffuses through the skin and thus the device 1 enables a broad new approach of non-invasive diagnostics.

Examples of possible analytes: Lactate, Glucose, Creatinine, Bilirubin, Urea, Ammonia, Opioid, Cocaine, Cortisone, Hydrocortisone, Caffeine, drugs (to control the taking of medication)

FIGS. 36 to 46 show a further embodiment of the device 1/probe head 10 according to the invention.

Again, the probe head 10 comprises a diffusion chamber (also denoted as microdialysis chamber) 100 that is delimited by a membrane 30 for contacting the skin 2 of a patient P, wherein the diffusion chamber 100 comprises an inlet 101 as well as an outlet 102 for feeding a perfusion medium 3 into the diffusion chamber 100 and for discharging it out of the diffusion chamber 100. The probe head 10 further comprises a first conduit 110 (e.g. a capillary) being in flow connection with the inlet 101 as well as second conduit 111 (e.g. a capillary) being in flow connection with the outlet 102. Via said second conduit 111, the outlet 102 is connected to an analyzing means 20 for measuring the concentration of an analyte (e.g. glucose) in a perfusion medium 3, which analyte diffused through the membrane 30 in a first state of the latter, as well of the analyte in the perfusion medium 3, when the analyte diffused through the membrane 30 in a second state of the membrane, wherein the permeability of the membrane 30 with respect to said analyte differs in said two states such that the two concentrations of the analyte differ.

The probe head 10 may be used with the device 1 described in conjunction with FIG. 16. Further, all probe heads 10 described herein may be used in conjunction with the device shown in FIG. 51. The device 1 shown in FIG. 51 corresponds to the device of FIG. 16, with the difference that the device 1 according to FIG. 51 comprises an additional vacuum pump 204 connected via a pressure regulator 118 to the waste container 203 for receiving the analyzed dialysate. The pressure generated by the pump 204 can be measured by a pressure measurement device 205. The reagent fluid countainer could also be connected to this additional vacuum pump 204 via a pressure regulator 118 instead of the air compressor/compressed air line 120.

Further, the probe head 10 of FIGS. 36 to 46 comprises a body 11 that is preferably formed out of molded PDMS. The body 11 comprises a preferably circular recess 100 forming said diffusion chamber 100 on a front side of the body 11 facing away from a rear side of the body 11 on which said conduits 110, 111 are arranged. The recess 100 is covered by a light switchable membrane 30 as described herein, particularly an amphiphilic co-network mentioned above.

As the hydrophilic domain of the membrane 30 is e.g. made of PDMS, one can also bond the membrane 30 onto the body 11 of the probe head 10 with a surface treatment with oxygen plasma. The membrane 30 could be also bonded with UV curable resist.

Furthermore, the diffusion chamber 100 comprises a plurality of posts 113 for supporting the membrane 30. Said posts 113 may be formed by a grid structure 113 (e.g. of the type shown in FIG. 54 as a micrograph).

FIGS. 47 to 50 shows a further embodiment of the probe head 10 according to the invention wherein a microfluidic chip 201 (analyzing means 20), that may be designed as described above, is integrated into the probe head 10.

Here, the probe head 10 comprises (from top to bottom) again a membrane 30 (which may a suitable membrane described herein), e.g. in the form of an rectangular layer, for contacting the skin 2 of a person P (the contact surface of the membrane 30 is the shown upper side of the membrane 30 in FIG. 47), a layer (body) 11 that is preferably formed out of molded PDMS forming a diffusion chamber 100 comprising a plurality of posts (e.g. a grid structure) 113 for supporting the membrane 30, a scattering layer 300 that is preferably formed out of molded PDMS for uniformizing the membrane excitation light coming from fibers 260 for guiding light needed to switch the membrane 30 as described herein, a light guide plate 301 that is preferably formed out of molded PDMS and preferably consists of or comprises spherical mirrors for reflecting light with 90° with a density of the square of the distance to the fibers 260 for correcting the decrease of the intensity of the light emitted from the fibers 260, a mirror layer 302 that is preferably formed out of molded PDMS for reflecting all the light emitted from the fibers 260 into the light guide plate 301 onto the membrane 30 made of a hollow cavity supported by a plurality of posts 303 (e.g. in the form of a grid structure 303), an optical shield 304 that is preferably formed out of molded PDMS mixed with a black light absorbing dye for absorbing light and preventing light to reach the microfluidic chip (or analyzing means) 201 as described herein, fibers 252a for guiding visible light (VIS) from the fluorescence chambers 25 and 27 as well as fibers 253a for guiding UV light to the fluorescence chambers 25 and 27 (see also above), and another optical shield 305 that is preferably formed out of molded PDMS mixed with a black light absorbing dye for again preventing light to reach the microfluidic chip (or analyzing means) 201 and enclosing the embedded probe head 10.

The probe head 10 further comprises a conduit 240 (e.g. capillary) for guiding reagent fluid 4 to reagent inlet 21 of chip 201 (the dialysate inlet 22 is connected to the diffusion chamber 100), as well as a conduit (e.g. capillary) 110 for guiding the perfusion medium 3 into the diffusion chamber 100, and a conduit (e.g. capillary) 280 for drawing off the measured analyte from the chip 100.

The above-described components of the probe head 10 are particularly designed in the form of layers that are stacked on top of each other, as can be seen in FIG. 47. Further, FIGS. 52 and 53 show molds for a microfluidic chip of the kind shown in FIGS. 17 and 47, with regions for the probed volume 251, the visible light (VIS) fluorescence emission collection fibers 252 and the fibers for ultra-violet UV fluorescence excitation light 253

Furthermore, FIG. 54 shows an SEM micrograph of a diffusion (microdialysis) chamber 100 of the kind shown in FIG. 47 with the grid structure 113 for supporting the adjacent membrane 30.

Further. FIG. 55 shows the 3D flow streamlines inside the diffusion chamber of the probe head shown in FIGS. 36 to 46, the flow being laminar;

FIG. 56 shows a cross-section of a model of the diffusion chamber 100 of the kind in FIG. 38, 44 showing the local dialysate extraction fraction having values between 0 (no substance extracted) and 1 (same concentration as in the blood). Shown are the results from a 3D Finite Element Method with a high permeability of the membrane 30.

FIG. 57 shows the same simulation as FIG. 56, but with a lower permeability of the membrane 30

FIG. 58 shows the total dialysate extraction fraction at the outlet of the diffusion chamber of the kind shown in FIGS. 38 and 44 as determined from the theory or from a FEM simulation. The two results are linearly proportional $R^2=1$. This means that the simulated probe head 10 even with more complicated laminar flow pattern can be well explained by the theory.

FIG. 59 shows that in the application range the dialysate extraction fraction at the outlet of the diffusion chamber of the kind shown in FIGS. 38 and 44 is linearly proportional to the membrane permeability for both the theory $R^2=0.9996$ and the simulation $R^2=0.9998$.

FIG. 60 shows that as predicted from the theory, the dialysate extraction fraction at the outlet of the diffusion chamber of the kind shown in FIGS. 38 and 44 does not depend on the height if the diffusion chamber in the 3D FEM simulation. There is no significant correlation between the chamber height and the dialysate extraction fraction. The differences in the dialysate extraction fraction between the different points come from computing errors. This means that the if the height of the diffusion chamber 100 changes, it does not influence the dialysate extraction fraction nor the measurement, and FIG. 61 shows the dialysate extraction fraction of a probe head of the kind of FIG. 36-46 measured with two different states, once exposed with white light, once exposed with UV light. This shows that exposing the membrane 30 to UV light or white light controls the dialysate extraction fraction.

REFERENCES

[1] de Courten, D., Baumann, L., Scherer, L. J., & Wolf, M. (2012). Opto-Fluidic Chip for Continuous Inline Monitoring of Glucose with Kinetic Enzymatic Fluorescence Detection. Procedia Engineering, 47, 1203-1206.

[2] N. Bruns, J. Scherble, L. Hartmann, R. Thomann, B. Iván, R. Mülhaupt, J. C. Tiller, Macromolecules, 2005, 38, 2431-2438.

The invention claimed is:

1. Device for measuring the concentration of an analyte in the blood or tissue of an animal or a human, which analyte passively diffused through the skin of said animal or human, wherein for measuring said concentration the device comprises a membrane (30) comprising at least a first and a second permeability with respect to said analyte, wherein the first permeability for said analyte differs from the second permeability for said analyte, wherein the membrane (30) is designed to be switched between a first state, in which said membrane (30) comprises said first permeability with respect to said analyte, and a second state, in which said membrane (30) comprises said second permeability with respect to said analyte, such that the mass flow rate of the analyte that diffuses through said membrane (30) when the membrane (30) resides in the first state differs from the mass flow rate of the analyte that diffuses through said membrane (30) when the membrane (30) resides in the second state, and wherein the device (1) comprises an analyzing means (20) for measuring the concentration of said analyte in the blood or tissue of said animal or said human, wherein said analyzing means (20) is designed to measure a first concentration of the analyte diffused through the membrane (30) residing in the first state, and wherein said analyzing means (20) is designed to measure a second concentration of the analyte diffused through the membrane (30) residing in the second state.

2. Device according to claim 1, characterized in that said means (20) comprises a probe head (10) for contacting the skin of said animal or said human, wherein the probe head (10) comprises said membrane (30).

3. Device according to claim 1, characterized in that the device comprises a switching means (40) for switching said membrane (30) between said two states, wherein for switching said membrane (30) between said two states, the switching means is designed to one of:
   irradiate the membrane (30) with electromagnetic radiation,
   irradiate the membrane (30) with light,
   apply an electric and/or a magnetic field to the membrane (30),
   change the pH-value of a medium contacting said membrane (30),
   change the temperature of the membrane (30), or
   exert a pressure and/or a shear stress on said membrane (30).

4. Device according to claim 3, characterized in that said switching means comprises a light source (40) designed to irradiate said membrane (30) with light.

5. Device according to claim 4, characterized in that the switching means comprises a light guide (401) for guiding said light of the light source (40) towards the membrane (30).

6. Device according to claim 2, characterized in that the probe head (10) comprises a diffusion chamber (100) adjacent to said membrane (30) for receiving said analyte.

7. Device according to claim 6, characterized in that the diffusion chamber (100) comprises an inlet (101) for feeding a perfusion medium (3) into the diffusion chamber (100), as well as an outlet (102) for discharging said perfusion medium (3) out of the diffusion chamber (100).

8. Device according to claim 7, characterized in that the analyzing means (20) is connected to said outlet (102), so that said perfusion medium (3) together with the respective analyte can be transported to the analyzing means (20).

9. Device according to claim 1, characterized in that said membrane (30) comprises a photochromic compound.

10. Device according to claim 1, characterized in that the membrane (30) comprises a spirobenzopyran moiety or a spirooxazine moiety, wherein particularly the membrane (30) is formed out of a polycarbonate coated or grafted with a compound or a polymer comprising said spirobenzopyran moiety or spirooxazine moiety.

11. Device according to claim 1, characterized in that said membrane (30) comprises an amphiphilic network comprising a spirooxazine moiety or a spirobenzopyran moiety.

12. Device according to claim 2, characterized in that the analyzing means (20) comprises a microfluidic chip (201) configured for measuring said concentrations using a fluorescence measurement, which microfluidic chip (201) is integrated into the probe head (10).

13. Device according to claim 12, characterized in that the microfluidic chip (201) is arranged on top of a diffusion chamber (100) of the probe head (10) on a side facing away from the membrane (30).

14. Method for measuring the concentration of an analyte in the blood or tissue of an animal or a human, the method comprising the steps of:
letting the analyte diffuse through a membrane (30) comprising a first permeability with respect to said analyte, and
letting said analyte diffuse through said membrane (30) comprising a second permeability with respect to said analyte, wherein the first permeability differs from the second permeability, and
measuring a first concentration of the analyte diffused through the membrane (30) comprising the first permeability, and measuring a second concentration of the analyte diffused through the membrane comprising the second permeability, and determining the concentration of said analyte in the blood or tissue using said first and second concentration.

15. Method for measuring the concentration of an analyte in the blood or tissue of an animal or a human, comprising the steps of:
letting the analyte diffuse through a membrane (30) comprising a first permeability with respect to said analyte, and
letting said analyte diffuse through a further membrane comprising a second permeability with respect to said analyte, wherein the first permeability differs from the second permeability, and
measuring a first concentration of the analyte diffused through the membrane comprising the first permeability, and measuring a second concentration of the analyte diffused through the further membrane comprising the second permeability, and determining the concentration of said analyte in the blood or tissue using said first and second concentration.

16. Device for measuring the concentration of an analyte in the blood or tissue of an animal or a human, which analyte passively diffused through the skin of said animal or human, wherein for measuring said concentration the device comprises a membrane comprising a first permeability with respect to the analyte and a further membrane comprising a second permeability with respect to said analyte, wherein the first permeability for said analyte differs from the second permeability for said analyte such that the mass flow rate of the analyte that diffuses through the membrane differs from the mass flow rate of the analyte that diffuses through the further membrane, and wherein the device (1) comprises an analyzing means (20) for measuring the concentration of said analyte in the blood or tissue of said animal or said human, wherein the analyzing means is designed to determine the concentration $C_{g,body}$ of the analyte in the blood of the animal or human with help of measuring a concentration of the analyte $C_{ml}$ for the first permeability and a concentration $C_{mh}$ of the analyte for a lower second permeability and calculating $C_{ml}C_{mh}/(C_{ml}-C_{mh})$.

17. Device for measuring the concentration of an analyte in the blood or tissue of an animal or a human, which analyte passively diffused through the skin of said animal or human, wherein for measuring said concentration the device comprises a membrane (30) comprising at least a first and a second permeability with respect to said analyte, wherein the first permeability for said analyte differs from the second permeability for said analyte, wherein the membrane (30) is designed to be switched between a first state, in which said membrane (30) comprises said first permeability with respect to said analyte, and a second state, in which said membrane (30) comprises said second permeability with respect to said analyte, such that the mass flow rate of the analyte that diffuses through said membrane (30) when the membrane (30) resides in the first state differs from the mass flow rate of the analyte that diffuses through said membrane (30) when the membrane (30) resides in the second state, and wherein the device (1) comprises an analyzing means (20) for measuring the concentration of said analyte in the blood or tissue of said animal or said human, wherein the analyzing means is designed to determine the concentration $C_{g,body}$ of the analyte in the blood of the animal or human with help of measuring a concentration of the analyte $C_{ml}$ for the first permeability and a concentration $C_{mh}$ of the analyte for a lower second permeability and calculating $C_{ml}C_{mh}/(C_{ml}-C_{mh})$.

* * * * *